United States Patent
Lesher

(10) Patent No.: US 11,675,341 B2
(45) Date of Patent: *Jun. 13, 2023

(54) METHOD AND SYSTEM FOR PERFORMING QUALITY CONTROL ON A DIAGNOSTIC ANALYZER

(71) Applicant: SYSMEX CORPORATION, Kobe (JP)

(72) Inventor: Scott Lesher, Lincolnshire, IL (US)

(73) Assignee: SYSMEX CORPORATION, Hyogo (JP)

(*) Notice: Subject to any disclaimer, the term of this patent is extended or adjusted under 35 U.S.C. 154(b) by 262 days.

This patent is subject to a terminal disclaimer.

(21) Appl. No.: 16/992,310

(22) Filed: Aug. 13, 2020

(65) Prior Publication Data

US 2020/0371507 A1    Nov. 26, 2020

Related U.S. Application Data

(63) Continuation of application No. 16/248,608, filed on Jan. 15, 2019, now Pat. No. 10,775,777, which is a
(Continued)

(51) Int. Cl.
*G05B 19/41* (2006.01)
*G16H 40/40* (2018.01)
(Continued)

(52) U.S. Cl.
CPC .   *G05B 19/41875* (2013.01); *G01N 35/00613* (2013.01); *G01N 35/00871* (2013.01);
(Continued)

(58) Field of Classification Search
CPC .... G05B 19/41875; G05B 2219/32368; G05B 2219/33326; G01N 35/00613;
(Continued)

(56) References Cited

U.S. PATENT DOCUMENTS 5,532,941 A    7/1996  Lin
5,835,384 A   11/1998  Lin
(Continued)

FOREIGN PATENT DOCUMENTS

EP    1107159 A2    6/2001
JP   H9-502811 A    3/1997
(Continued)

OTHER PUBLICATIONS

The Communication pursuant to Article 94(3) EPC dated May 21, 2021 in a counterpart European patent application No. 17163279.7.
(Continued)

*Primary Examiner* — Michael J Brown
(74) *Attorney, Agent, or Firm* — Crowell & Moring LLP

(57) ABSTRACT

A method for performing quality control on a diagnostic analyzer includes receiving control measurement values from each of a plurality of diagnostic analyzers. A quality control measurement value is received from a target diagnostic analyzer. The quality control measurement value is compared with statistical criteria associated with the plurality of quality control measurement values received from the plurality of diagnostic analyzers. A comparison result is communicated to a user interface associated with the target diagnostic analyzer.

21 Claims, 23 Drawing Sheets

Related U.S. Application Data continuation of application No. 15/087,604, filed on Mar. 31, 2016, now Pat. No. 10,197,993.

(51) Int. Cl.
   *G16Z 99/00* (2019.01)
   *G05B 19/418* (2006.01)
   *G01N 35/00* (2006.01)

(52) U.S. Cl.
   CPC .............. *G16H 40/40* (2018.01); *G16Z 99/00* (2019.02); *G01N 2035/00653* (2013.01); *G01N 2035/00881* (2013.01); *G05B 2219/32368* (2013.01); *G05B 2219/33326* (2013.01)

(58) Field of Classification Search
   CPC ... G01N 35/00871; G01N 2035/00653; G01N 2035/00881; G01N 35/00623; G16Z 99/00; G16H 40/40
   USPC ......................................................... 700/109
   See application file for complete search history.

(56) References Cited

U.S. PATENT DOCUMENTS

| | | | |
|---|---|---|---|
| 5,918,191 | A | 6/1999 | Patel |
| 6,748,337 | B2 | 6/2004 | Wardlaw et al. |
| 8,029,732 | B2 | 10/2011 | Le |
| 10,197,993 | B2 | 2/2019 | Lesher |
| 10,775,777 | B2 * | 9/2020 | Lesher ............ G01N 35/00871 |
| 2002/0128801 | A1 | 9/2002 | Okuno et al. |
| 2003/0154044 | A1 | 8/2003 | Lundstedt et al. |
| 2006/0129345 | A1 | 6/2006 | Pavin et al. |
| 2007/0027648 | A1 | 2/2007 | Kowata |
| 2009/0199052 | A1 | 8/2009 | Yamaguchi et al. |
| 2011/0022343 | A1 | 1/2011 | Cembrowski |
| 2013/0024130 | A1 | 1/2013 | Zahniser |
| 2014/0249500 | A1 | 9/2014 | Estes |

FOREIGN PATENT DOCUMENTS

| | | |
|---|---|---|
| JP | 2001-229291 A | 8/2001 |
| JP | 2002340906 A | 11/2002 |
| JP | 2003057248 A | 2/2003 |
| JP | 2003279583 A | 10/2003 |
| JP | 2007-034604 A | 2/2007 |
| JP | 2009-181369 A | 8/2009 |
| JP | 2011-81837 A | 4/2011 |
| JP | 2013185975 A | 9/2013 |
| JP | 2014-521939 A | 8/2014 |
| JP | 2015135282 A | 7/2015 |
| JP | 2016-24194 A | 2/2016 |
| WO | 2013/016038 A1 | 1/2013 |

OTHER PUBLICATIONS

The Japanese Office Action dated Jan. 12, 2021 in a counterpart Japanese patent application No. 2017-034174.
Chinese Office Action dated Jul. 11, 2019 in a counterpart Chinese Application No. 201710194148.7.
The Japanese Office Action dated Sep. 13, 2022 in a counterpart Japanese patent application No. 2021-179089.
Chinese Office Action dated Jan. 31, 2023, in a counterpart Chinese patent application No. 202010401523.2.

* cited by examiner

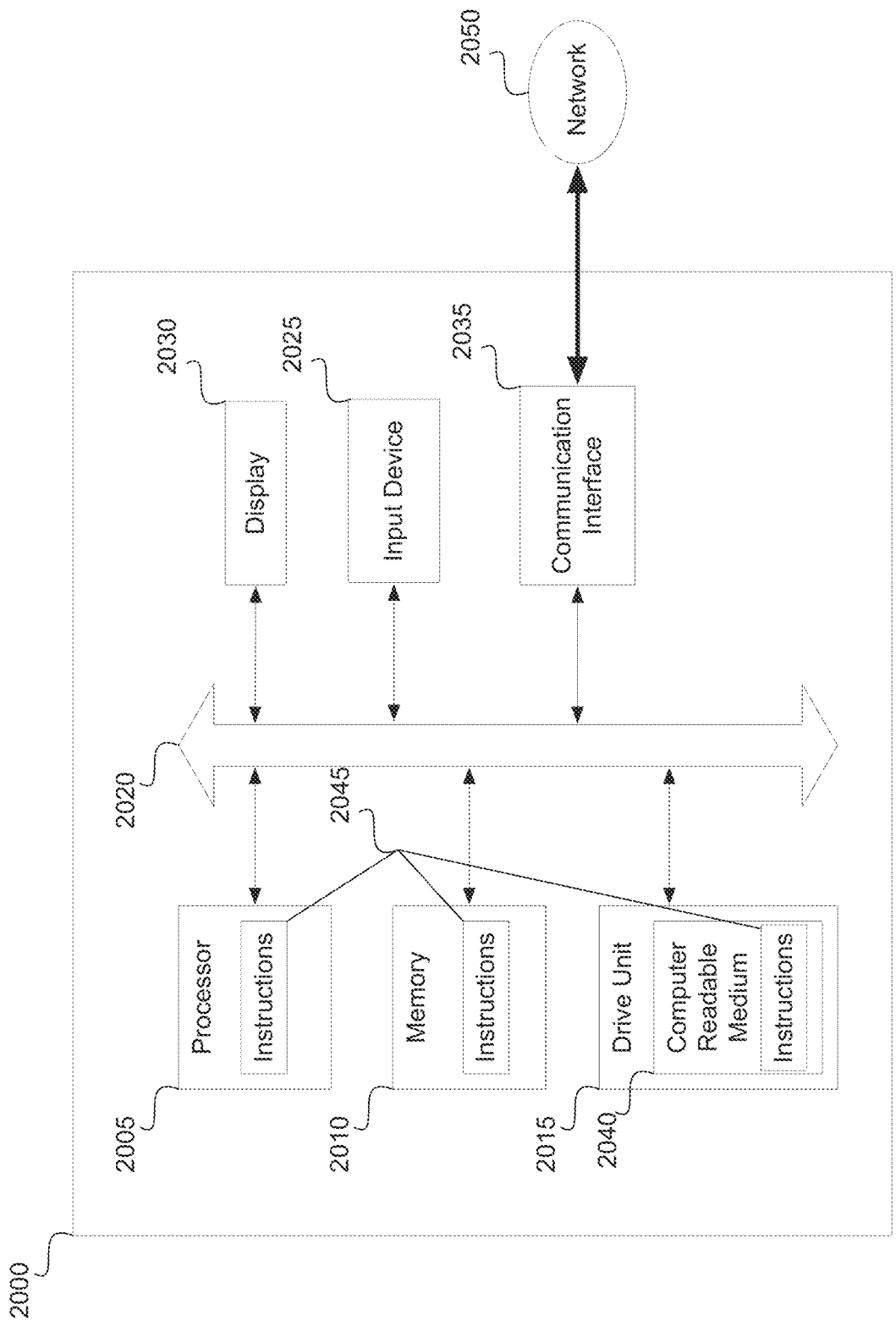

METHOD AND SYSTEM FOR PERFORMING QUALITY CONTROL ON A DIAGNOSTIC ANALYZER

RELATED APPLICATIONS

This application is a continuation under 35 U.S.C. § 120 of U.S. patent application Ser. No. 16/248,608, filed on Jan. 15, 2019, which is a continuation of U.S. patent application Ser. No. 15/087,604, filed on Mar. 31, 2016, and issued as U.S. Pat. No. 10,197,993 on Feb. 5, 2019, the contents of each of which are incorporated herein by reference in their entirety.

BACKGROUND i) Field

This application relates to diagnostic analyzer utilized in a medical setting. In particular, this application relates to a method and a system for performing quality control on a diagnostic analyzer.

ii) Description of the Related Art

Diagnostic analyzers, such as hematology analyzers are utilized to perform various measurements of the constituents of a blood sample. Such analyzers tend to be placed in hospitals and laboratories. For example, a given hospital may have several laboratories. Each laboratory may have any number of analyzers.

In a typical laboratory environment, one or more lab operators are required to run diagnostic test, change reagents, and tend to other maintenance related activities associated with the analyzers, such as calibration of the analyzers.

The skill level of a given operator may vary significantly, in which case the lab operator may not be familiar with quality control measurements on a given analyzer. For example, the operator may not have knowledge how to perform the quality control measurements or how to evaluate a result of the quality control measurement. The operator may use a quality control sample that is too old. Therefore, the operator may not accurately assess a condition of the analyzer and may not appropriately deal with problems that may have occurred in the analyzer.

Other problems known with operating problems faced by lab personnel will become apparent upon reading the descriptions of the various embodiments described below.

SUMMARY

In one aspect, a method for performing quality control on a diagnostic analyzer includes receiving control measurement values from each of a plurality of diagnostic analyzers. A quality control measurement value is received from a target diagnostic analyzer. The quality control measurement value is compared with statistical criteria associated with the plurality of quality control measurement values received from the plurality of diagnostic analyzers. A comparison result is communicated to a user interface associated with the target diagnostic analyzer.

In a second aspect, a method for performing quality control on a diagnostic analyzers, includes receiving a quality control measurement value from each of a plurality of diagnostic analyzers; receiving, from a target diagnostic analyzer, a quality control measurement value; and comparing the quality control measurement value received from the target diagnostic analyzer with statistical criteria associated with the plurality of quality control measurement values received from the plurality of diagnostic analyzers. When the quality control measurement value received from the target diagnostic analyzer conform to the statistical criteria, issuing a calibration verification certificate associated with the target diagnostic analyzer.

In a third aspect, a method for performing quality control on a diagnostic analyzer includes receiving sample measurement data associated with a plurality of patient samples from a target diagnostic analyzer. At least one mean value associated with at least one quantity of a constituent of the plurality of patient samples is determined based on the sample measurement data received from the target diagnostic analyzer. The at least one mean value is compared with statistical criteria associated with a plurality of different patient samples. When the at least one mean value does not conform to the statistical criteria, an indication is communicated to a user interface associated with the target diagnostic analyzer that a quality control measurement is required.

In a fourth aspect, a system for performing quality control includes a target diagnostic analyzer, a plurality of peer group diagnostic analyzers that are peers of the target diagnostic analyzer, and a central server in communication with the target diagnostic analyzer and the plurality of peer group diagnostic analyzers. The target diagnostic analyzer is configured to generate a quality control measurement associated with a quality control sample. The plurality of peer group diagnostic analyzers are configured to generate quality control measurements associated with quality control samples measured in the peer group diagnostic analyzers. The central server is configured to receive the quality control measurements from both the target diagnostic analyzer and the plurality of peer group diagnostic analyzers and to determine statistical criteria associated with the quality control measurements received from the plurality of peer group diagnostic analyzers. The central server compares the quality control measurement received from the target diagnostic analyzer with the statistical criteria and communicates a comparison result to a user interface associated with the target diagnostic analyzer.

In a fifth aspect, a server for performing quality control includes a processor in communication with a target diagnostic analyzer and a plurality of peer group diagnostic analyzers; and non-transitory computer readable media in communication with the processor. The non-transitory computer readable media includes instructions code that when executed by the processor causes the processor to receive the quality control measurements from both the target diagnostic analyzer and the plurality of peer group diagnostic analyzers and to compare the quality control measurement value received from the target diagnostic analyzer with statistical criteria associated with the plurality of quality control measurement values received from the plurality of peer group diagnostic analyzers. The instruction code also causes the processor to communicate a comparison result to a user interface associated with the target diagnostic analyzer.

In a sixth aspect, a diagnostic analyzer includes measurement hardware, a user interface, a communication interface, and a processor in communication with the measurement hardware, the user interface, and the communication interface. The measurement hardware is configured to measure constituent quantities of a quality control sample. The user interface is configured to indicate an operational status of the diagnostic analyzer. The communication interface is configured to facilitate data transfer between the diagnostic analyzer and a central server. The processor is configured to control the measurement hardware to measure a quantity of at least one constituent of the quality control sample and to communicate, via the communication interface, the measurement to the central server. The processor is further configured to receive, from the central server, an indication as to whether there is an issue with the measurement and update the user interface to indicate that there is an issue with the measurement. The processor receives one or more instructions from the central server for troubleshooting the issue with the measurement and displays, via the user interface, the one or more instructions.

In a seventh aspect, a diagnostic analyzer includes measurement hardware configured to measure constituent quantities of a quality control sample; a user interface; a communication interface configured to facilitate data transfer between the diagnostic analyzer and a central server; and a processor in communication with the measurement hardware, the user interface, and the communication interface. The processor is configured to receive, from the central server, statistical criteria associated with a plurality of quality control measurement values received from a plurality of diagnostic analyzers; control the measurement hardware to measure a quantity of at least one constituent of the quality control sample; compare the measurement value with the statistical criteria; and display a comparison result via the user interface.

In an eighth aspect, a method of operating a diagnostic analyzer includes controlling measurement hardware to measure a quantity of at least one constituent of a quality control sample; communicating, via a communication interface, a measurement value associated with the measured quantity to a central server; receiving, from the central server, an indication as to whether there is an issue with the measurement value; updating the user interface to indicate that there is an issue with the measurement value; receiving one or more instructions from the central server for troubleshooting the issue with the measurement value; and displaying, via a user interface, the one or more instructions.

BRIEF DESCRIPTION OF THE DRAWINGS

FIG. 2 illustrates exemplary startup operations that may be performed by a target diagnostic analyzer in a first laboratory 105a;

FIG. 20 illustrates a general computer system that may represent any of the computing devices referenced herein.

DETAILED DESCRIPTION

The embodiments disclosed below overcome the problems described above by basing the target values, the upper limits and the lower limits used for assessing whether a quality control measurement is normal on group data (e.g., group mean, bias, and coefficient of variation) associated with a large peer group of diagnostic analyzer such as 1000 analyzers or more. In the United States, Clinical Laboratory Improvement Amendments (CLIA) regulation requirements dictate that calibration verification on a diagnostic analyzer must be performed at least once every 6 months. Because most of the peer group diagnostic analyzers are well-calibrated, the group data obtained from the diagnostic analyzers is reliable. That is, the group data provides consistent and accurate values for the mean, upper limit and lower limit for the constituents in a quality control sample. This facilitates providing tighter limits for the total allowable error which results in more accurate measurements associated with patient samples.

Figure 1:
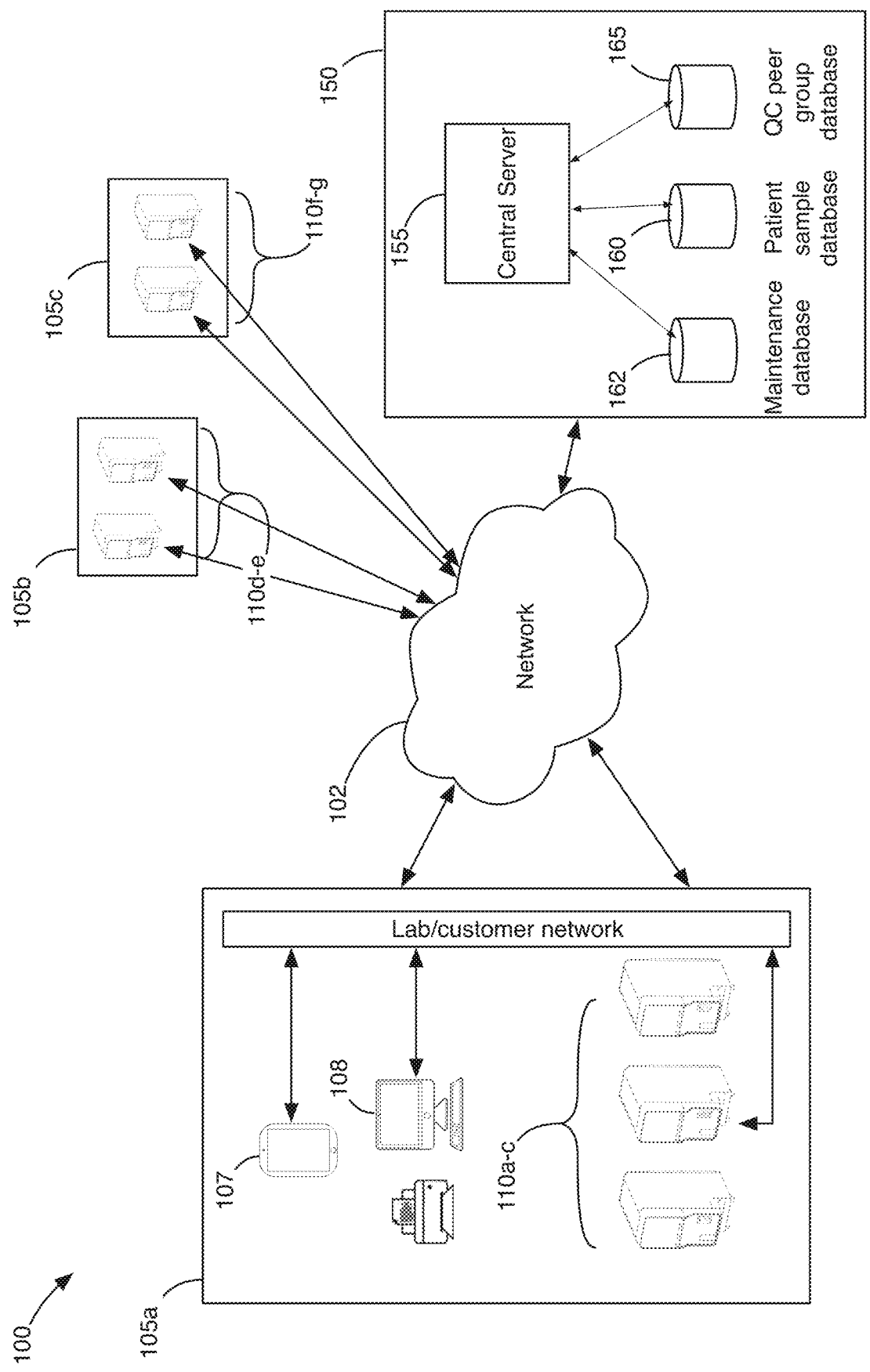
FIG. 1 illustrates an exemplary environment that includes a group of laboratories where diagnostic testing may be performed, and a central service provider that processes information received from the laboratories.

FIG. 1 illustrates an exemplary environment 100 that includes a group of laboratories 105a-c where diagnostic testing may be performed, and a central service provider 150 that processes information received from the laboratories 105a-c. Each laboratory 105a-c may include one or more diagnostic analyzers 110a-g that may be utilized to perform various diagnostics on patient blood samples. The diagnostic analyzers 110a-g may correspond to automated cell counters. Each of the diagnostic analyzers 110a-g includes measurement hardware for conducting measurement of quality control materials and patient samples. The measurement hardware includes: for example, one or more chambers for preparing a measurement sample by mixing a sample and a reagent; a white blood cell detector having a flow cell through which a WBC measurement sample flows; and a RBC detector. Operators within each laboratory 105 may tend to various diagnostic related duties, such as preparing hematology tests, changing reagents in the analyzers 110, verifying whether the analyzers 110a-g are calibrated, etc.

With respect to calibration verification, each laboratory 105a-c may be provided with different lots of quality control (QC) samples. The different lots of QC samples are prepared in a controlled environment where precise quantities of different constituents are mixed together in a large batch. The batch is then poured into different sample vials to provide a group of sample vials having similar quantities of the different constituent substances. The groups of sample vials are broken into lots, such as lot A, lot B, etc. The constituents in each lot are measured by highly accurate equipment to provide assay target values associated with the constituents of the lot. The different lots of QC samples may be sent to various laboratories so that the different laboratories are verify the operation of diagnostic analyzers based on nearly identical QC samples. For example, each of the laboratories 105a-c may receive a number of QC samples from lot A.

Each lot includes QC samples with different levels or amounts of constituents. The different levels are utilized to verify the accuracy and precision of a given analyzer. For example, a first QC sample may have a low concentration or level of a given constituent and a second QC sample may have a high concentration or level of the same constituent. The different levels facilitate verifying that the analyzer can measure accurately over a range of constituent levels.

In some implementations, the lab operators may be provided with tablet computers 107 (hereinafter tablet), such an Apple iPad®, a tablet running an Android® operating system, or a different tablet operating a different operating system. The tablets provide a centralized way to access the status of any number of diagnostic analyzers 110 operating within the laboratory 110.

In addition, or alternatively, each laboratory 110a-c may be equipped with a central computer 108 that is in communication with diagnostic analyzers 110a-g within the laboratory 110a-c and the central server 155. The central computer 108 may gather measurement data generated by the analyzers 110a-g and forward the information to the central server 155. The central computer 108 may also be provided with a user interface through which an operator may review the measurement data associated with patient samples and either approve the data for release to, for example, a hospital or doctor, or reject the data. The user interface may also facilitate viewing and prang various reports related to the accuracy of the diagnostic analyzers 110a-g.

The central service provider 150 includes a central server 155 that receives and processes the information generated by the diagnostic analyzers 110a-g in the laboratories 105a-c via a network 102. In general, the central server 155 stores measurements data associate with QC samples and patient samples generated by the diagnostic analyzers 110a-g. The central server 155 compares the measurement data against various statistical criteria to assess the operating condition of the diagnostic analyzers 110a-g.

Figure 2:
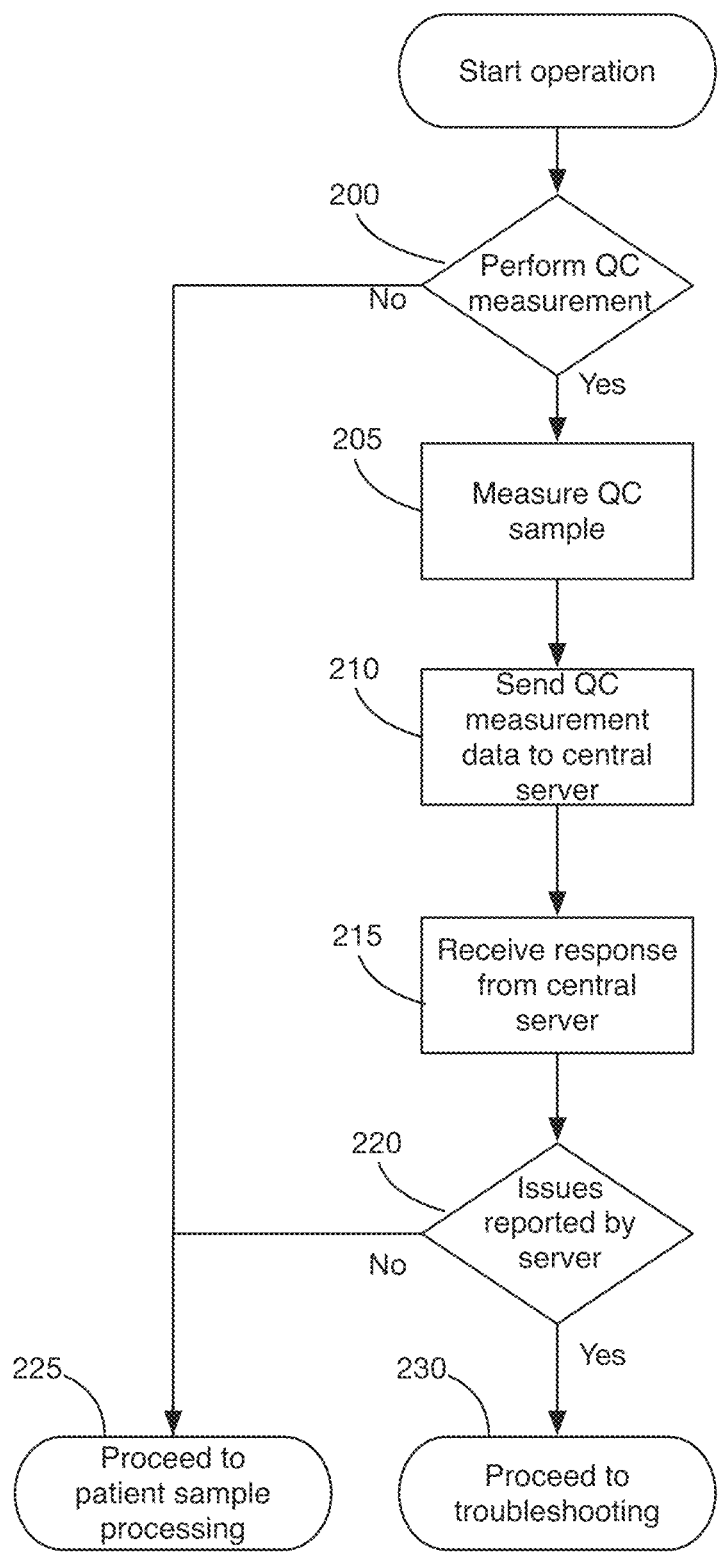

FIG. 2 illustrates exemplary startup operations that may be performed by a target diagnostic analyzer 110a in a first laboratory 105a. It should be understood that the procedures described below may apply to any diagnostic analyzer 110a-g that operates within the environment 100. Additionally, in some implementations, the procedures may be realized by executing instruction code stored in a non-transitory form of computer readable medium by a system such as the target diagnostic analyzer 110a, the central servicer 155, or any other system described herein for causing the system to perform the various procedures.

At block 200, a quality control (QC) measurement may be performed on the target diagnostic analyzer 110a. For example, the target diagnostic analyzer 110a may be powered on. A message may be displayed on the target diagnostic analyzer 110a instructing an operator to select a QC sample of a given level from, for example, lot A. The instructions may further instruct the operator to shake the QC sample for a specified amount of time to evenly distribute the constituents of the QC sample. In some implementations, the display of the target diagnostic analyzer 110a may show a countdown timer or the like to help the operator know that he has mixed the QC sample for the specified time. Afterwards, the operator may insert the QC sample into the target diagnostic analyzer 110a.

At block 205, the target diagnostic analyzer 110a may measure the quantities of the constituents of the QC sample.

At block 210, the target diagnostic analyzer 110a may communicate the measured values to the central server 155. In addition, the target diagnostic analyzer 110a may communicate information that identifies the type and model of the target diagnostic analyzer 110a. Other information communicated may include the lot from which the QC sample was obtained.

At block 215, the target diagnostic analyzer 110a may receive a response associated with the previously communicated QC measurements from the central server 155.

If at block 220, the response indicates that the QC measurements were normal, then at block 225, the target diagnostic analyzer 110a may be permitted to proceed to patient sample processing.

If at block 220, the response indicates that there were issues associated with the QC measurements, then at block 230, the target diagnostic analyzer 110a may proceed to a troubleshooting phase.

Figure 3:
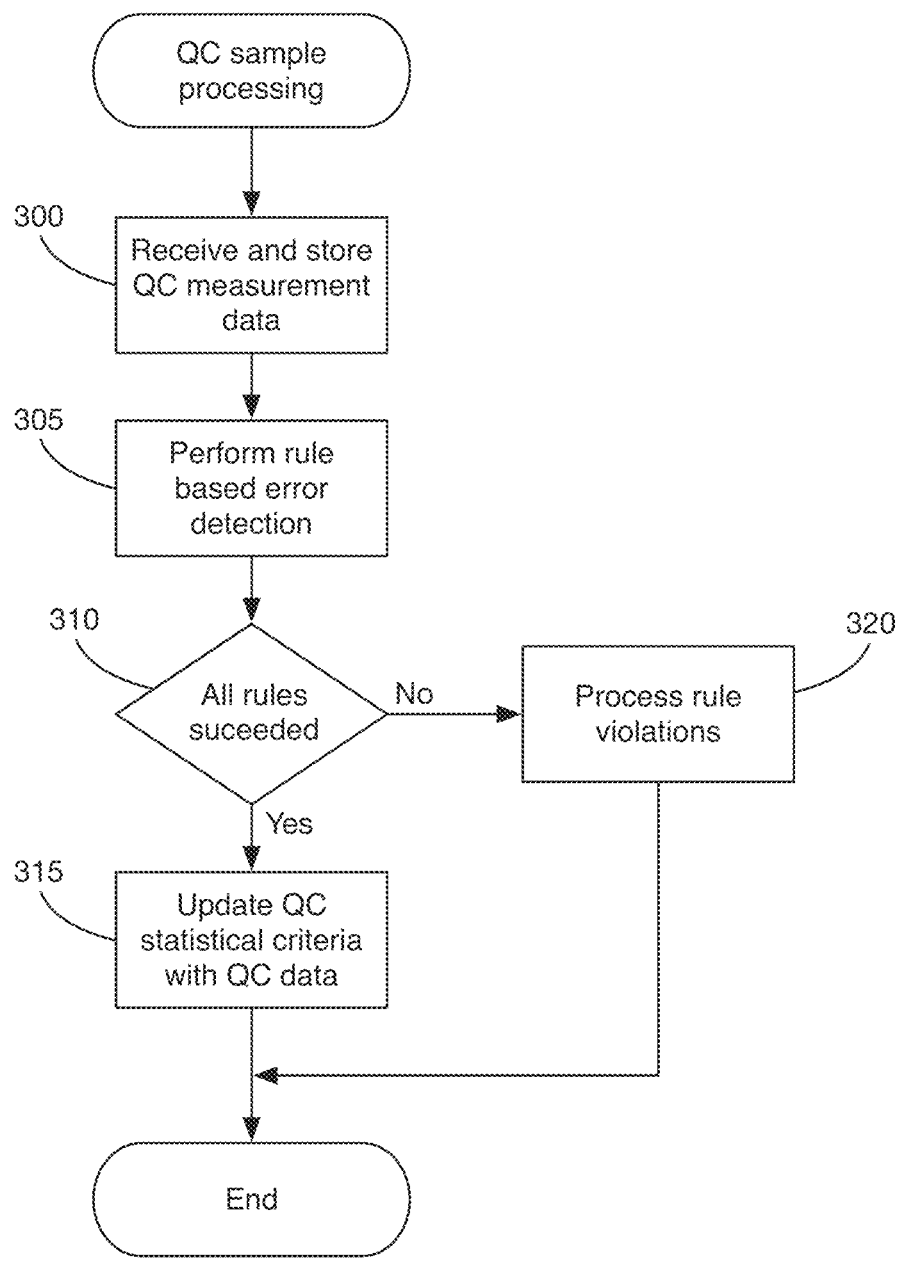
FIG. 3 illustrates exemplary operations that may be performed by a central server in processing measurements associate with a QC sample.

FIG. 3 illustrates exemplary operations that may be performed by the central server 155 in processing measurements associate with a QC sample. At block 300, QC measurements may be communicated from the target diagnostic analyzer 110a to the central server 155. The central server 155 may store the QC measurements to a database such as the QC peer group database 165, illustrated in FIG. 1.

The QC peer group database 165 may be configured to store records associated with QC measurements received from any diagnostic analyzer 110a-g in communication with the central server. Table 1 below illustrates an exemplary record of the QC peer group database 165.

TABLE 1

| Model/ Serial No. | Lot | Level | RBC | HGB | ... | MCH |
|---|---|---|---|---|---|---|
| XN-10 14364 | 6011 | L1 | 2.25 | 5.95 | | 26.45 |

Referring to Table 1, each record may specify the model and serial number of the diagnostic analyzer 110a-f from which the QC measurements were received, the lot of the QC sample associate with the QC measurements, the level, and QC measurements associated with the constituents of the QC sample. Other information may be included in the record.

At block 305, the central server 155 may apply a set of rules against the received QC measurement to determine whether there may be any issues related to the QC measurement.

Figure 4:
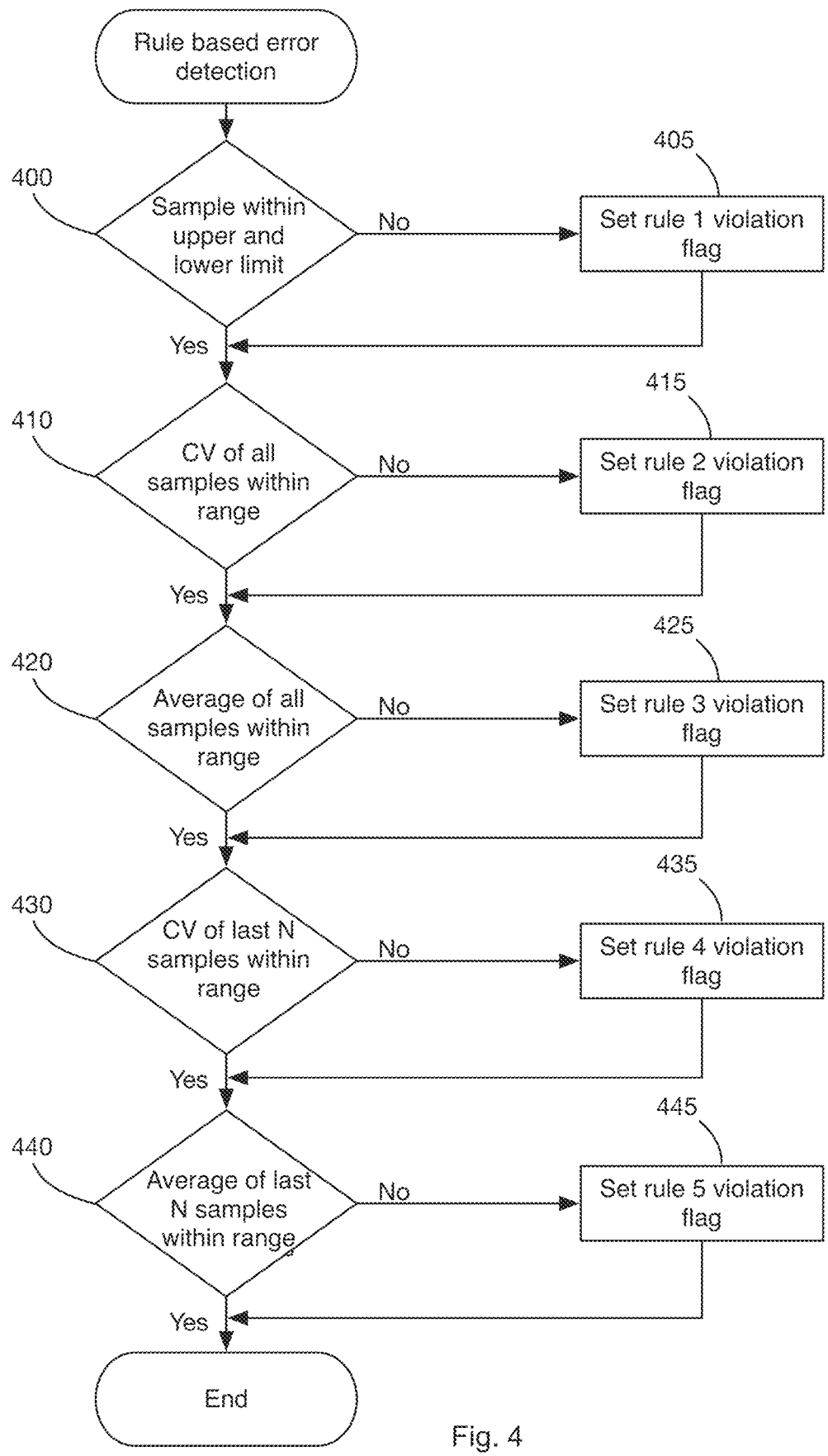
FIG. 4 illustrates exemplary rules that may be applied in FIG. 3.

FIG. 4 illustrates exemplary rules that may be applied at block 305. In general, the rules compare the received QC measurement against a set of statistical criteria to detect potential problems with the QC measurement. The statistical criteria are generated based on QC measurements associated with QC samples from the same lot and level as the QC measurement being considered, that are received from other diagnostic analyzers 110b-f that may be of a same type as the target diagnostic analyzer 110a. For example, if the QC measurement received from target diagnostic analyzer 110a is a level 1 QC sample taken from lot 6011, the statistical criteria may be based on level 1 QC samples taken from lot 6011 that were analyzed by diagnostic analyzers of the same type as the target diagnostic analyzer 110a. Table 2 illustrates exemplary statistical criteria that may be generated based on QC measurements received from other diagnostic analyzers 110b-f.

TABLE 2

| Sample | | | Group | | | |
|---|---|---|---|---|---|---|
| Lot | Type | Constituent | Upper Limit | Lower Limit | Mean | CV |
| 6011 | L1 | WBC | 3.27 | 2.67 | 3.00 | 2% |
| 6011 | L2 | WBC | 7.39 | 6.43 | 6.87 | 1.8% |
| 6011 | L3 | WBC | 17.16 | 15.22 | 16.26 | 1.8% |
| 6011 | L1 | RBC | 2.42 | 2.19 | 2.3 | 2% |
| 6011 | L2 | RBC | 4.43 | 4.09 | 4.26 | 1.8% |
| 6011 | L3 | RBC | 5.37 | 4.95 | 5.16 | 1.8% |
| ... | | | | | | |

Referring to Table 2, statistical criteria for each constituent of each level of each lot may include the upper and lower limits or quantities (i.e., group range) for a given constituent along with the average quantity (i.e., group mean) and coefficient of variation (i.e., group CV) of a given constituent for the QC measurements received from the peer group (diagnostic analyzers 110 a-f).

Referring to the flow diagram of FIG. 4, if at block 400 the central server 155 determines that the constituents of the QC sample are not within the total allowable error upper limit ($TE_a$ UL) and lower limit ($TE_a$ LL) associated with the peer group, then at block 405 a flag may be set to indicate a rule 1 violation. $TE_a$ UL and $TE_a$ LL are defined as follows:

$TE_a$UL=Group Mean+($TE_a$*Group Mean), $TE_a$LL=Group Mean−($TE_a$*Group Mean), Where $TE_a$=EBQCL+(n*group CV), EBQCL is a value to determine total error allowable (TEa) limits using a performance goal, allowable variation, and measured test method variability for each analyte concentration, and n is table driven. More specifically, the EBQCL is defined as follows:

EBQCL=(performance goal-bias)/CV, where the performance goal is a Six Sigma method of probability to achieve goal. The performance goal is set to provide 99.4% probability control runs would be within limits when the test method is stable and unchanged. This would be 4 sigma quality. Overall for all parameters and levels there is around a 3% false control rejection which is about perfect. The allowable bias and CV are determined based on quality control measurement data collected from, for example, more than 600 analyzers over a period more than 500 days.

If at block 410 the central server 155 determines that the coefficient of variation associated with the quantity of each constituent across all QC sample measurements of the same lot and level received from the target diagnostic analyzer 110a are not within a range around the group CV for a given constituent, then at block 405 a flag may be set to indicate a rule 2 violation. For example, if the coefficient of variations associated with different values of all QC samples measured are greater than, for example, one to two times the group CV, a rule 2 violation may be determined.

If at block 420 the central server 155 determines that the mean of the quantity of each constituent across all QC sample measurements of the same lot and level received from the target diagnostic analyzer 110a are not within a range around the group mean for the given constituent, then at block 425 a flag may be set to indicate a rule 3 violation. For example, if the mean values associated with the different values of all QC samples measured are greater than, for example, two to three standard deviations, a rule 3 violation may be determined.

If at block 430 the central server 155 determines that the coefficient of variation associate with the quantity of each constituent across the last N QC sample measurements of the same lot and level received from the target diagnostic analyzer 110a are not within a range around the group CV for the given constituent, then at block 435 a flag may be set to indicate a rule 4 violation. For example, if the coefficient of variations associated with different values of the last N QC samples are greater than, for example, three to four times the group CV, a rule 4 violation may be determined.

If at block 440 the central server 155 determines that the mean of the quantity of each constituent across the last N QC sample measurements of the same lot and level received from the target diagnostic analyzer 110a are not within a range around the group mean for the given constituent, then at block 445 a flag may be set to indicate a rule 5 violation. For example, if the mean values associated with the different values of the last N QC samples are greater than, for example, three to four standard deviations, a rule 5 violation may be determined.

Figure 5B:
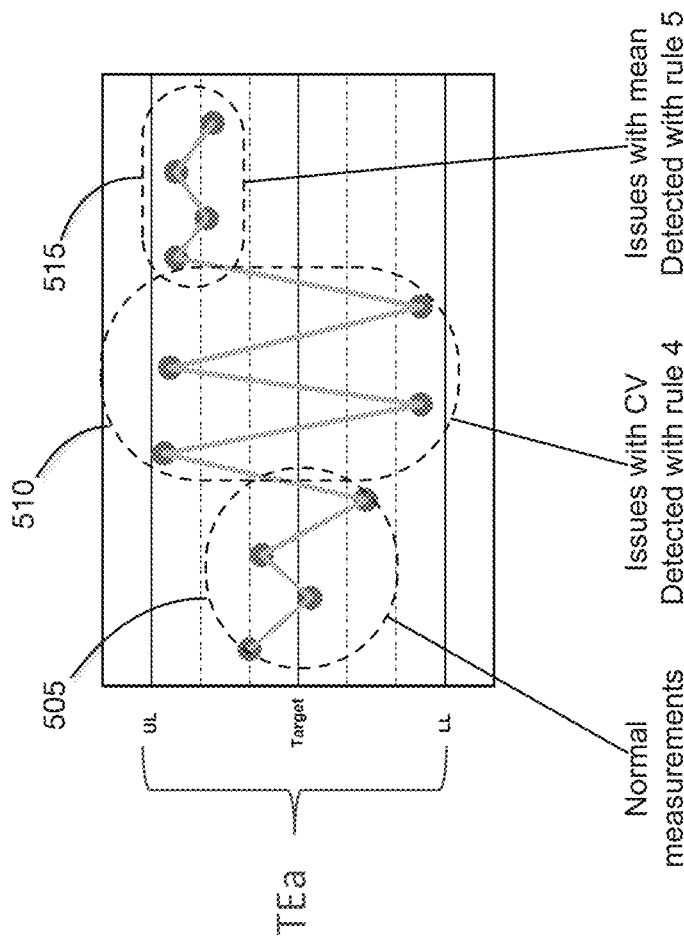
FIGS. 5A and 5B illustrates application of rules of FIG. 4.
Figure 5A:
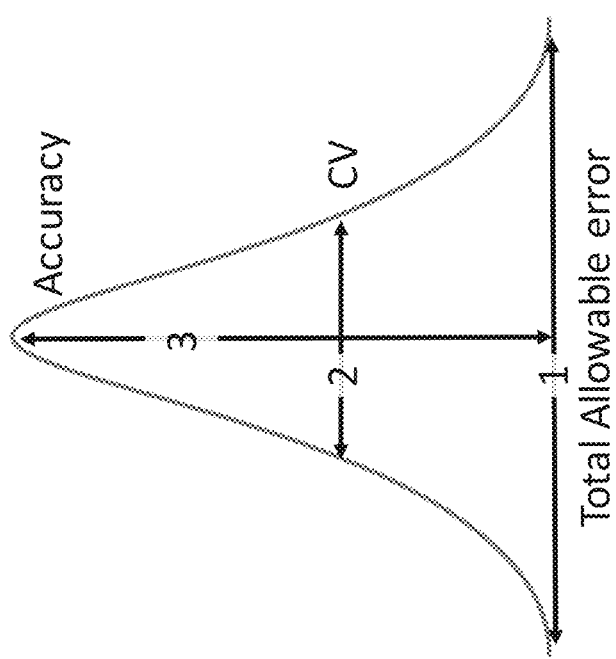

Application of the rules above is better understood with reference to FIGS. 5A and 5B. FIG. 5A illustrates the application of rules one, two, and three. Rule 1 checks whether the quantity of each constituent in a QC measurement received from the target diagnostic analyzer 110a falls within upper and lower limits of the group upper and lower limits. That is, rule 1 checks whether the QC measurement associated with the quantities of various constituents falls within the $TE_a$ UL and $TE_a$ LL described above.

Rules 2 and 3 respectively check whether the CV associated with the quantity and the mean quantity of each constituent of all QC measurements received from the target diagnostic analyzer 110a fall within the group CV and the group mean for a given constituent. Rules 2 and 3 facilitate determining long term shifts in the CV and mean for QC measurements generated by the target diagnostic analyzer 110a. A long term shift may, for example, be attributed to degradation in a QC sample over time or due to some gradual degradation in the performance of the target diagnostic analyzer 110a.

Referring to FIG. 5B, rules 4 and 5 respectively check whether the CV associated with the quantity and the mean quantity of each constituent of the last N QC measurements received from the target diagnostic analyzer 110a fall within a range around the group CV and the group mean for a given constituent. N may, for example, be set to four. In this case, the CV and mean of the target diagnostic analyzer 110a are associated with the last four QC measurements received from the target diagnostic analyzer 110a.

As illustrated in FIG. 5B, rules 4 and 5 facilitate detecting sudden shifts between normal QC measurements 505 to measurements 510 having a CV beyond the range of the group CV and/or measurements 515 having a mean beyond the range of the group mean. Such shifts may, for example, be attributed to a component failure of some kind in the target diagnostic analyzer 110a or perhaps improper setup of the target diagnostic analyzer 110a, 110b by an inexperienced operator.

As described below, knowledge of which rules were flagged facilitates selecting determining a proper course of action in resolving an issue with the target diagnostic analyzer 110a.

Returning to FIG. 3, if at block 310, the QC measurement successfully passed all the rules in FIG. 4, then at block 315, a record associated with the QC measurement may be added to the QC peer group database 165.

The statistical criteria may be updated to reflect the newly inserted QC measurement. In some implementations, the statistical criteria may be updated as each new QC measurement is added to the QC peer group database 165. In other implementations, the statistical criteria may be updated at a set period. For example, the statistical criteria may be updated on a daily or weekly basis. The statistical criteria may be updated at different interval. The QC measurement received from the target diagnostic analyzer may be compared with the most recently updated version of the statistical criteria.

In this regard, the statistical criteria compared against a given QC measurement may be generated by the central server 155 based on the group peer data collected during a predetermined period before the central server 155 receives the QC measurement. For example, the same group mean and group CV may be used to verify QC measurements measured throughout a given day. In alternate implementations, the statistical criteria may be updated immediately with newly received QC measurements that successfully pass the various rules.

Figure 6B:
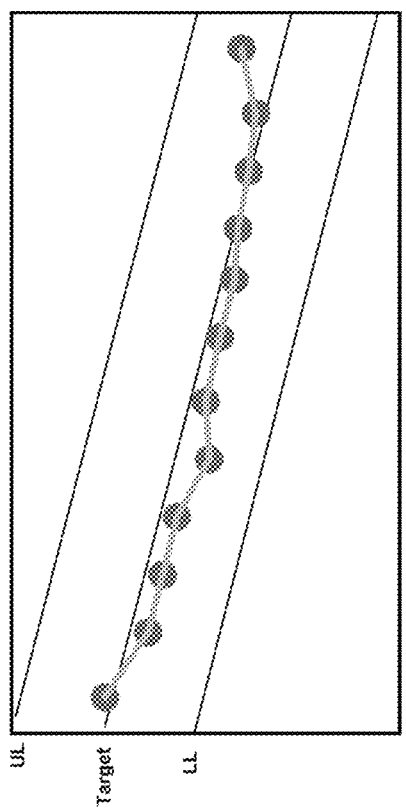
FIGS. 6A and 6B illustrate one of the benefits that results from generating statistical criteria based on group QC measurements.
Figure 6A:
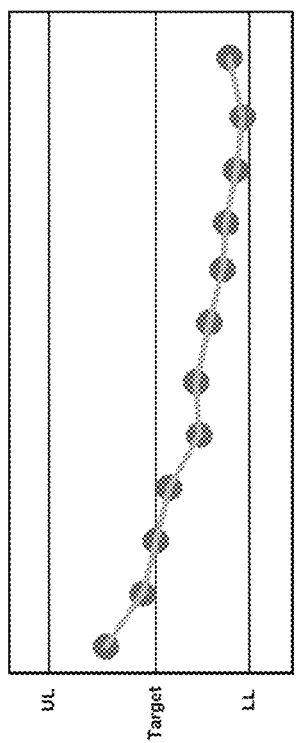

FIGS. 6A and 6B illustrate one of the benefits that results from generating statistical criteria based on group QC measurements. FIG. 6A illustrates QC measurements from a given diagnostic analyzer drifting lower over time. The drift may be the result of aging of a given QC sample, which is to be expected. In other words, the drifting does not necessarily indicate a problem of any sort with the diagnostic analyzer and may simply be normal given the age of the QC sample. Under ordinary circumstances, the total allowable error would need to be set so as to accommodate the wide variation in the values of normal QC measurements over the useful life of a QC sample.

However, setting the range for the total allowable error too high could prevent detection of actual issues with the QC measurements. For example, the expected value for a QC measurement associated with a new QC sample might be near the upper limit. But do to either an issue with the QC sample or the diagnostic analyzer, the actual QC measurement may be near the lower limit of the range. Such an issue would not be detected if the total allowable error too high.

One way to overcome this issue is to adjust the total allowable error to track the aging effects of the QC sample. FIG. 6B illustrates the same set of QC measurements in FIG. 6A and upper and lower limits that track lower over time to take into consideration the effects of normal aging of the QC sample. In this case, the upper and lower limits correspond to a percentage difference from a target value that is the target of the QC measurement. For example, the total allowable error may be set to ±10% of a target value. The target value is in turn based on the group mean value, which varies over time because all members of the group are using the same lot. That is, the group mean will change because the QC samples being run through the other diagnostic analyzers 110b-f are expected to exhibit the same aging characteristics as the QC sample being run through the target diagnostic analyzer 110a. Thus, the issue in FIG. 6A of setting the total allowable error too high is overcome by narrowing the total allowable error and adjusting the target range over time to match the group mean.

Returning to FIG. 3, if at block 310, one or more of the rules detected an issue with the QC measurement, then at block 320, steps may be taken to resolve the issue. In this case, the QC measurement may be excluded from the plurality of control measurement values from which the statistical criteria is determined.

Figure 7A:
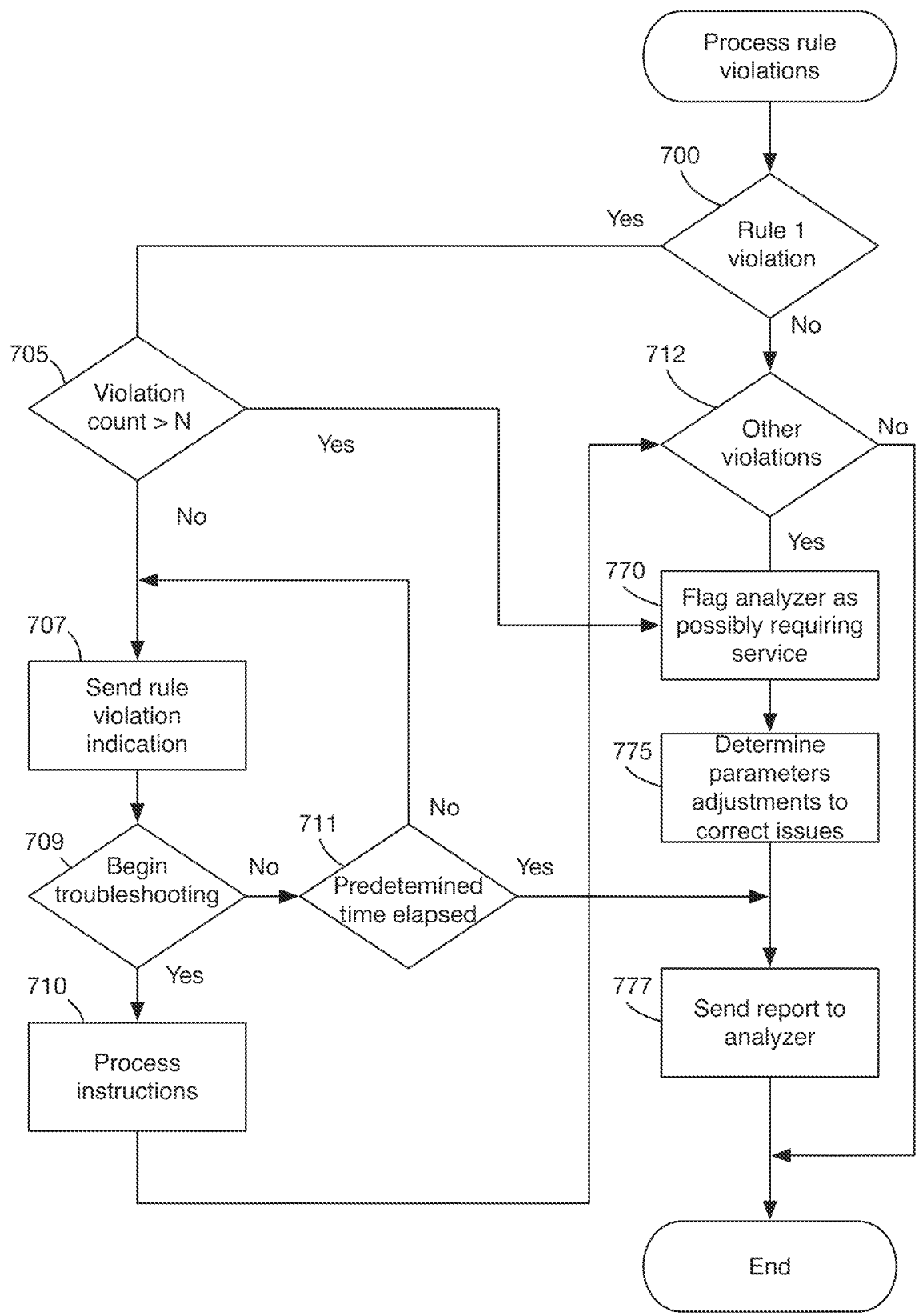
FIG. 7A illustrates exemplary operations for processing rule violations detected in FIG. 4.
Figure 7B:
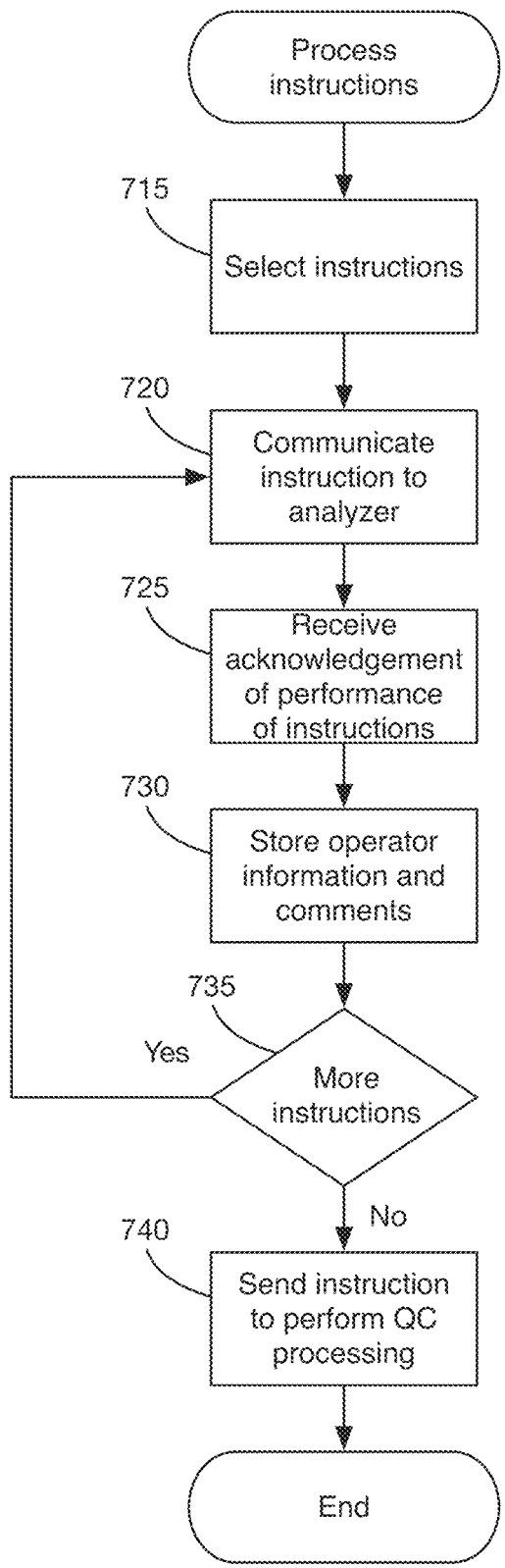
FIG. 7B illustrates exemplary instruction processing procedures that may be performed by the central server.

FIGS. 7A and 7B illustrate exemplary operations for processing rule violations detected in FIG. 4. The processing procedures are better understood with reference to the exemplary instruction process flow illustrated in FIG. 7C and the exemplary user interface screens illustrated in FIGS. 8-13, which may be displayed and/or updated on the central computer 108 and/or the target diagnostic analyzer of the laboratory 105a responsive to the procedures in FIGS. 7A and 7B. FIG. 7D illustrates exemplary operations performed by the target diagnostic analyzer 110a in cooperation with the operations of FIGS. 7A and 7B performed by the central server 155.

As noted above, a violation of rule 1 indicates that a given QC measurement is beyond the total allowable error. Violations of rule 1 occur suddenly as opposed to violations of rules 2-5, which are determined after having received a number of QC measurements. For example, a rule 1 violation may occur because the operator retrieved a QC sample from the incorrect lot. The operator may not have prepared the QC sample for measurement (e.g., may not have shaken the QC sample). A clog in a measurement portion of the target diagnostic analyzer 110a may have developed.

Referring to FIG. 7A, at block 700, if a rule 1 violation has occurred, and the number of consecutive times the rule 1 violation has occurred is below a limit (see block 705), then at block 707 the central server 155 may send a rule 1 violation indication to the central computer 108 of the laboratory 105a.

Figure 8:
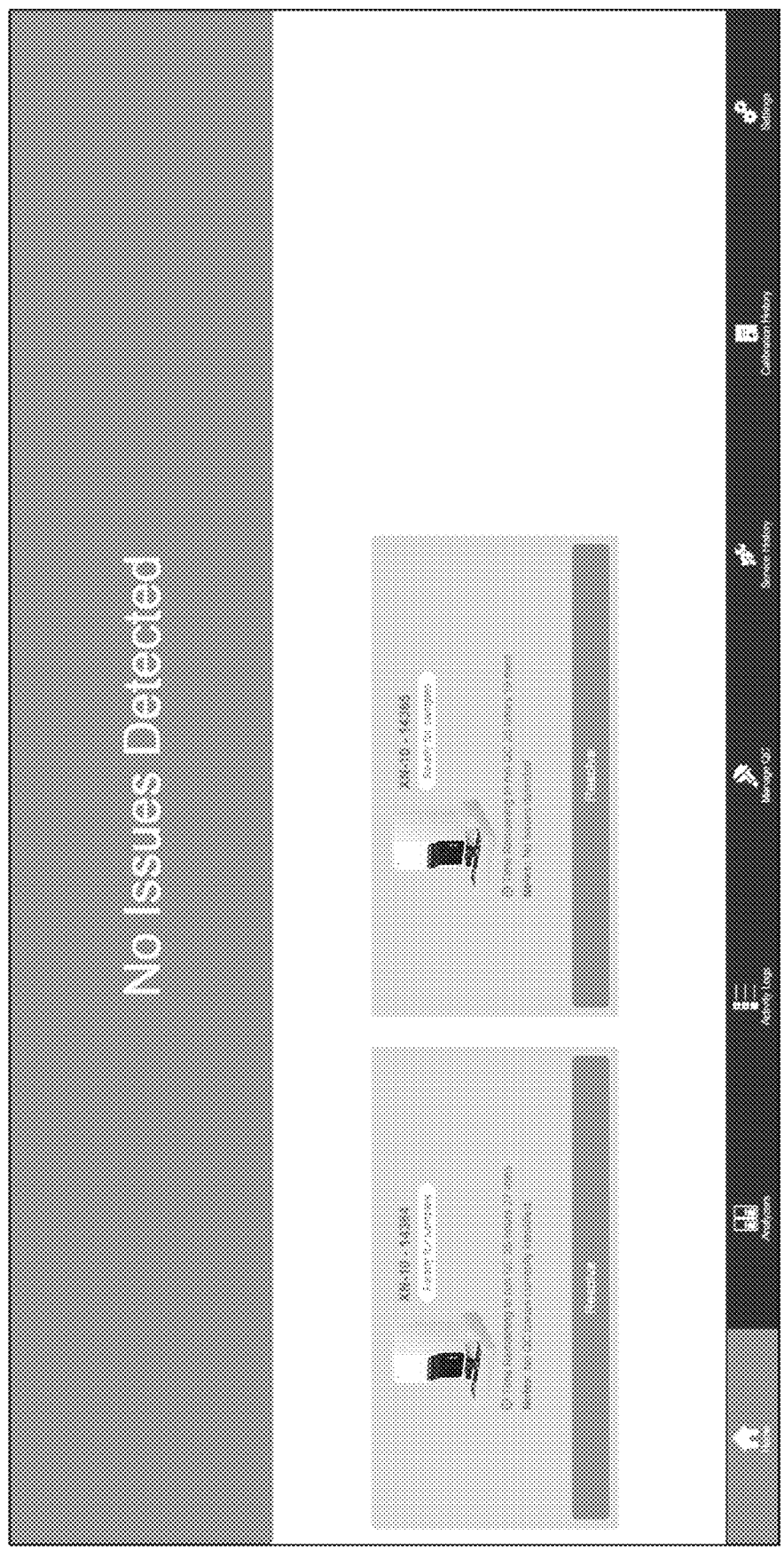
FIGS. 8-13 illustrate exemplary user interface screens that may be displayed and/or updated on a central computer of the laboratory in response to receiving an instruction from the central server.

FIG. 8 illustrates an initial screen 800 that may be shown on the central computer 108 and/or on the tablet 107, which depicts two diagnostic analyzer status windows 805a, 805b. Each status window 805a, 805b may be associated with a different diagnostic analyzers 110a, 110b of the laboratory 105a and may report the operational status and other information associated with the diagnostic analyzer 110a, 110b. For example, both status windows 805a, 805b are associated with model XN-10 diagnostic analyzers 110a, 110b. Both status windows 805a, 805b indicate that the respective diagnostic analyzers 110a, 110b are ready to receive QC samples or a patient sample.

Various graphical elements may be utilized to indicate the operational status of a given diagnostic analyzer 110a, 110b. For example, a green fill color may be utilized to indicate that the associated diagnostic analyzer 110a, 110b is ready to receive sample. A yellow fill color may be utilized to indicate a warning of some kind. A red fill color may be utilized to indicate that the associated diagnostic analyzer 110a, 110b is off line and that the diagnostic analyzer 110a, 110b requires service.

Figure 9:
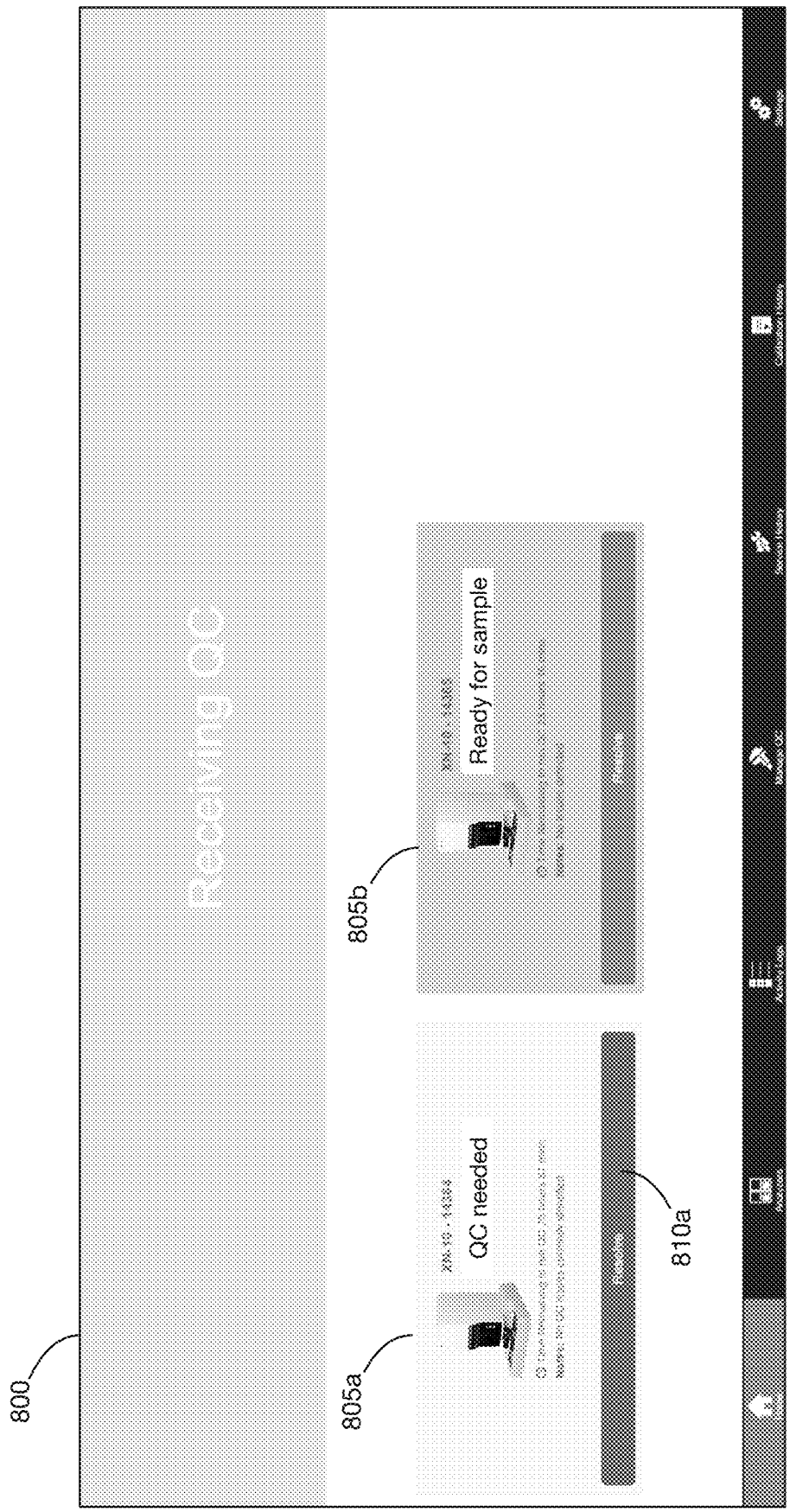

As illustrated in FIG. 9, upon receiving the rule 1 violation indication from the central server 155, the status window 805a associated with the target diagnostic analyzer 110a may be updated to reflect that an issue has been detected. For example, the status may be changed from "Ready for sample" to "QC needed" or "Trending issue." In some implementations, the fill color of the status window 805a may be changed to yellow to indicate that an issue has been detected. The status window 805a may include a button 810a for setting in motion a series of display events for resolving the issue with the target diagnostic analyzer 110a.

Figure 10:
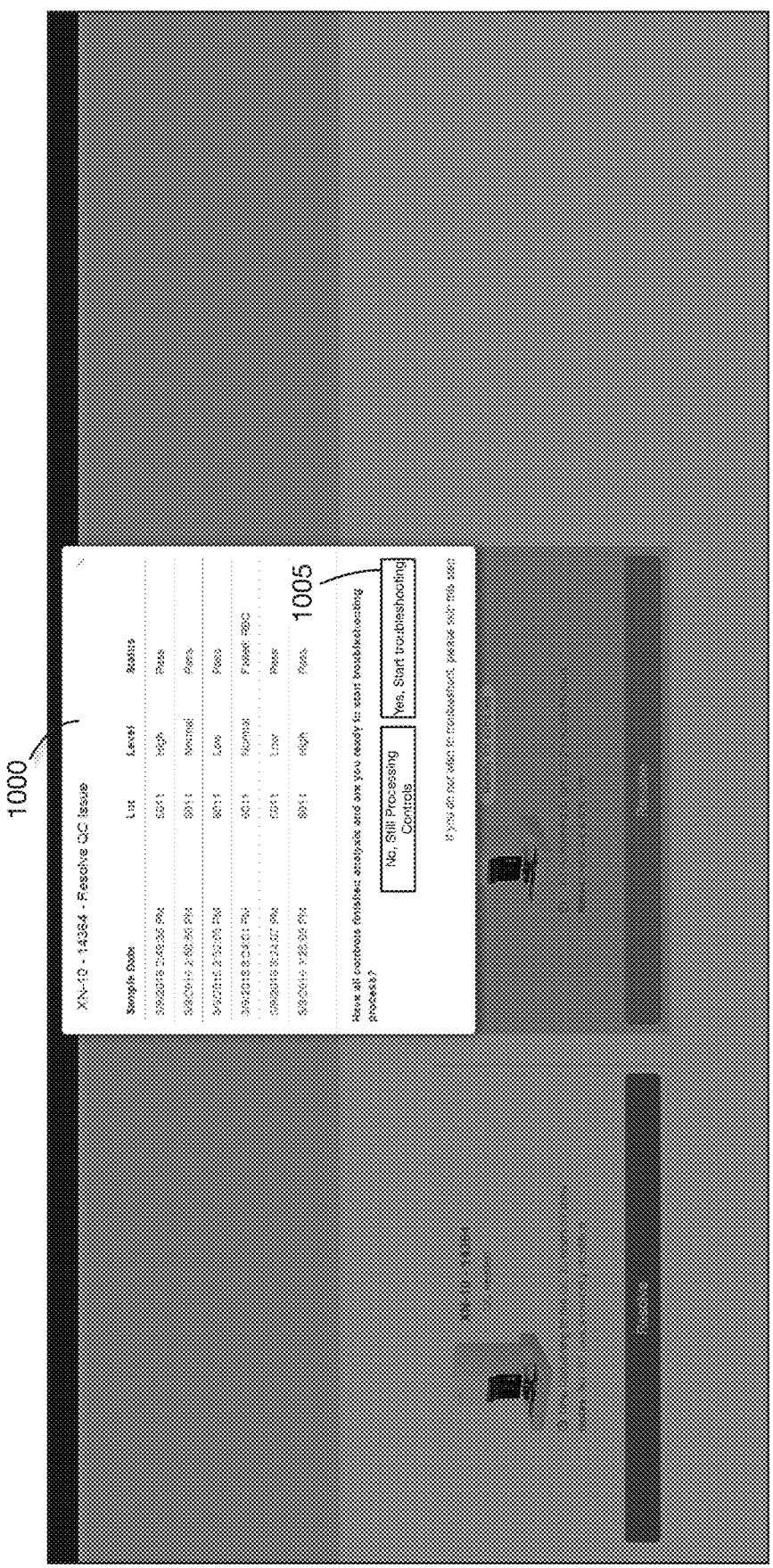

FIG. 10 illustrates an exemplary window 1000 that may be generated in response to user selection of the button 810a. The window 1000 includes information related to a number of previous QC measurements performed on the target diagnostic analyzer 110a along with the status of each measurement. According to the exemplary window, a QC measurement performed on Mar. 9, 2016 at 3:24:01 PM failed an RBC measurement. The exemplary window 1000 includes a troubleshoot button 1005 that may be selected by the operator to initiate the display of a series of troubleshooting instructions.

Returning to FIG. 7A, if at block 709 a troubleshooting request is communicated to the central server 155, then at block 710, instruction processing for having an operator execute instructions for resolving the issue may be performed by the central server 155. If at block 709, the troubleshoot button 1005 has not been selected by the operator, and if at block 711, a predetermined time has not passed, at block 707 the central server 155 may repeat from block 707 and send the rule 1 violation indication again. If at block 709 the predetermined time has passed, then the operations described below with respect to block 777 may be performed.

FIG. 7B illustrates an exemplary process flow that the central server 155 may follow in processing instructions. At block 715, instructions for resolving the issue may be selected by the central server 155. Selection of the instructions may be dependent on particular details related to the rule 1 violation, the lot being used, the number of times the violation has occurred, and/or based on other factors. For example, the instructions selected for resolving the first instance of a rule 1 violation may be different from the instructions selected for resolving the Nth instance of a rule 1 violation.

At block 720, a first instruction of the selected instructions may be communicated to the target diagnostic analyzer 110a. In addition, or alternatively, the instruction may be communicated to the central computer 108 and/or on the tablet 107 in the laboratory 105a that gathers measurement data from the target diagnostic analyzer 110a.

At block 725, the central server 155 may receive confirmation from the target analyzer 110a that the operation instructed in block 720 was performed. The central server 155 may also receive operator information that identifies the operator that performed the tasks specified in the instruction along with any comments that may have been provided by the operator in relation to performance of the tasks.

At block 730, the central server 155 may store the operator information to the maintenance log database 162.

At block 735, the central server 155 may determine whether there are additional instructions to send. If so, then the operations may repeat from block 720.

Figure 13:
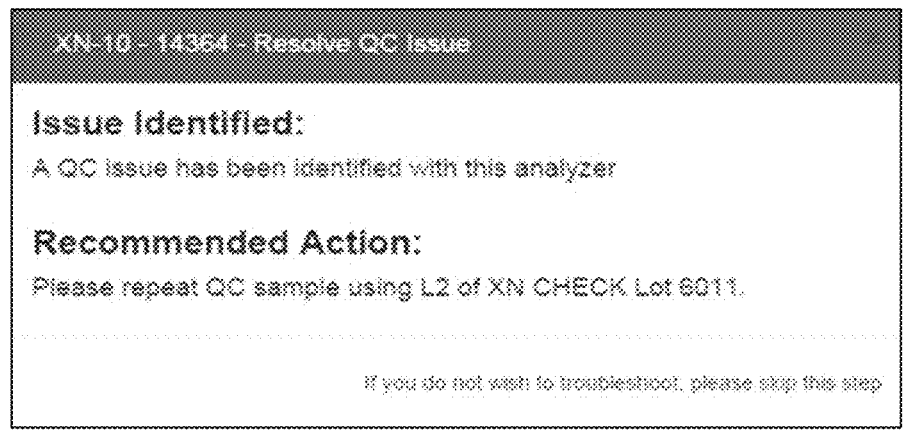

Upon receiving confirmation that the last instructions was performed, at block 740, the central server 155 may send an instruction to have the operator re-run a QC measurement, as illustrated in FIG. 13. If no further issues are detected afterwards, the status window 805a for the target diagnostic analyzer 110a that had the issue may be updated to reflect that the target diagnostic analyzer 110a is once again ready to receive patient samples.

On the other hand, if a subsequent QC measurement results in another rule violation, then the operations in FIG. 7A may repeat.

Figure 7C:
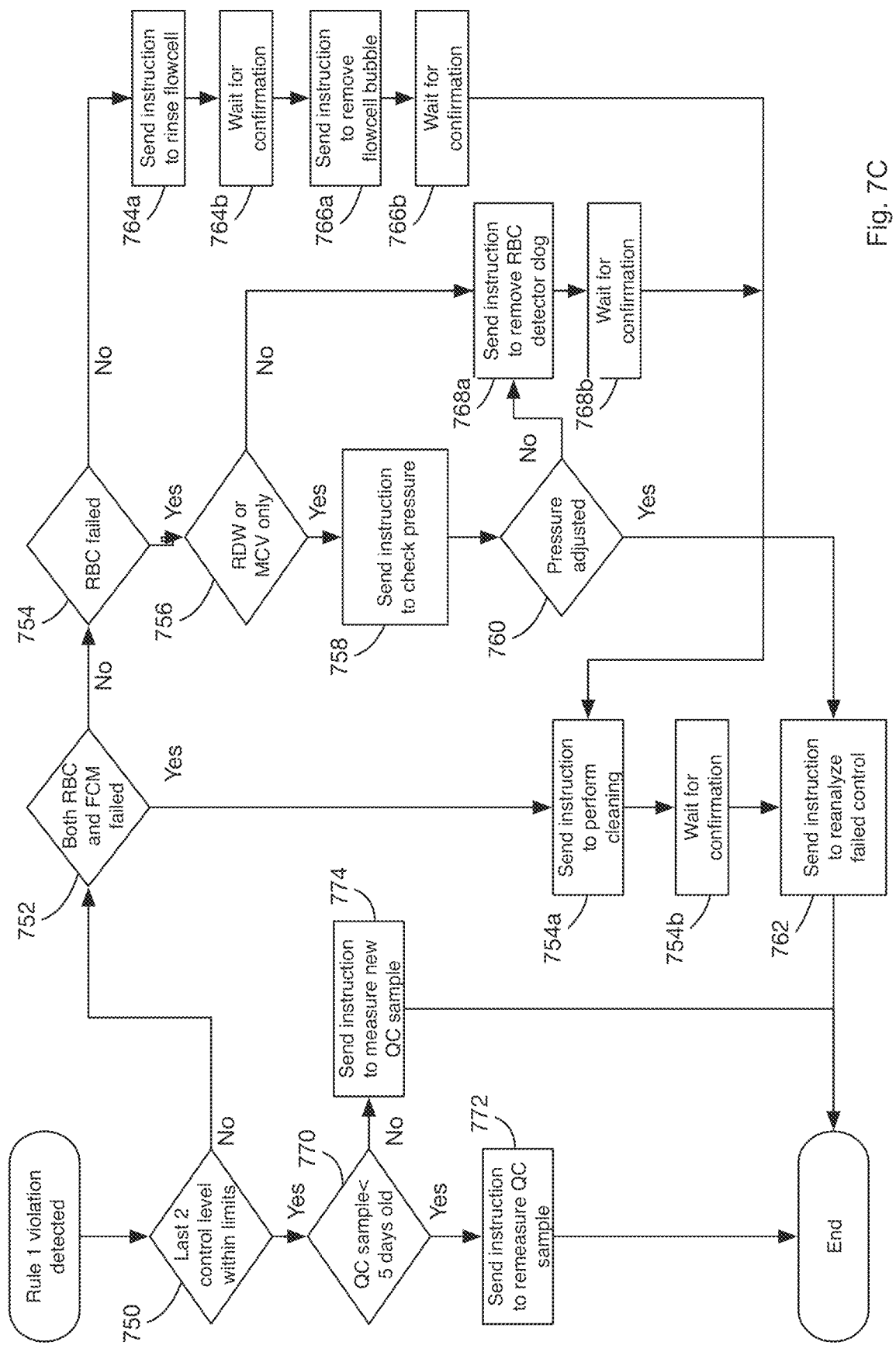
FIG. 7C illustrates an exemplary sequence of instructions that may be communicated by the central server in performing the processing procedures of FIG. 7B.
Figure 7D:
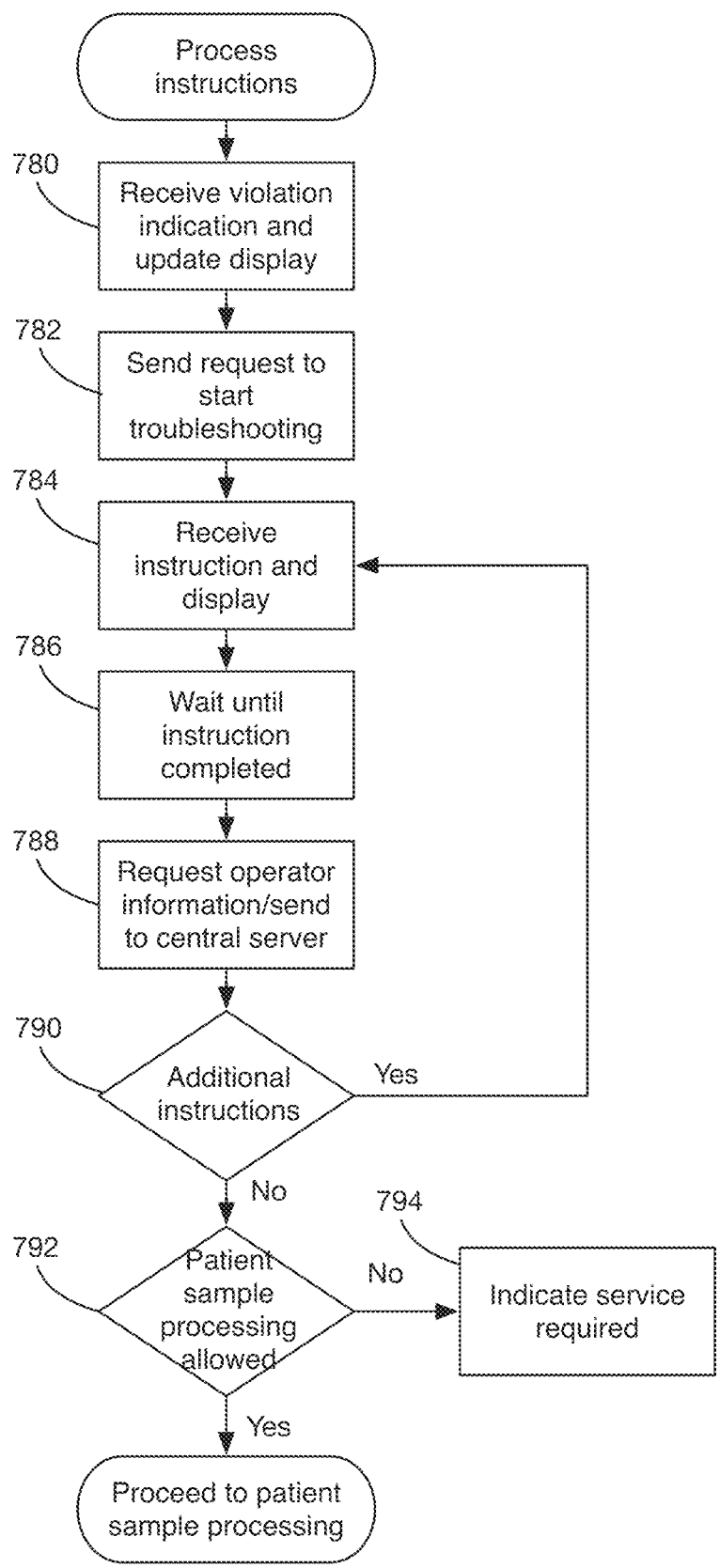
FIG. 7D illustrates exemplary operations of the target diagnostic analyzer performed in cooperation with the operations of FIGS. 7A and 7B performed by the central server.

FIG. 7C, illustrates exemplary instructions that may be processed via the flow of FIG. 7B. For example, after a rule 1 violation has been detected, if at block 750, the last 2 control levels were within limits, and if at block 770, the QC sample was, for example, less than five days old, the instruction selected at block 715 of FIG. 7B and communicated at block 720 of FIG. 7B may correspond to the instruction illustrated in block 772 to have the operator re-measure the QC sample. If at block 770, the QC sample was greater than five days old, the instruction selected at block 715 of FIG. 7B and communicated at block 720 of FIG. 7B may correspond to the instruction illustrated in block 774 to have the operator measure a new QC sample.

If at block 750, the last 2 control levels were not within limits, and at block 752, measurements associated with both RBC parameters, such as MCV (mean corpuscular volume) and RDW (RBC volume distribution width), and FCM parameters measurable by flow cytometer, such as scattered light intensity and florescent intensity, have failed at the same time, the instruction selected at block 715 of FIG. 7B and communicated at block 720 of FIG. 7B may correspond to the instruction to perform a cleaning operation illustrated at block 754a. The cleaning operation may include operations to clean all of the flow passages in the target diagnostic analyzer 110a by using chlorine-based detergent. The flow passages include one or more flowcells and RBC detector. Waiting for confirmation of the completion of the instructed operation, as illustrated in at block 754b, is performed by the central server 155 at block 725 of FIG. 7B. Finally, sending an instruction for re-analyzing a failed QC sample, as illustrated at block 762, is performed by the central server 155 at block 720 of FIG. 7B.

If according to blocks 752 and 754, only the measurement of the RBC parameters have failed, then at block 756, if either the RDW or MCV failed, an instruction for having the operator check the pressure of a measurement unit may be sent to the target diagnostic analyzer 110a, as illustrated at block 758, by the central server 155 at block 720 of FIG. 7B. If at block 760, the central server 155 receives confirmation from the target diagnostic analyzer 110a that an adjustment was made, then the instruction at block 762 for re-analyzing the failed QC sample may be sent to the target diagnostic analyzer 110a by the central server 155 at block 720 of FIG. 7B.

If according to blocks 752 and 754, only the measurement of FCM parameters have failed, then instructions for having the operator rinse the flowcell may be sent to the target diagnostic analyzer 110a at block 764a and confirmation of the completion of the instructed operation is waited for at block 764b. Then at block 766a, an instruction for having the operator remove the flowcell bubble may be sent to the target diagnostic analyzer 110a and confirmation of completion of the instructed operation is waited for at block 766b. The operations from 754a may be performed next.

As noted above, communication of each instruction to the target diagnostic analyzer 110a may be performed by the central server 155 at block 720 of FIG. 7B. Waiting until receiving a confirmation that the instructed operation is performed may be performed by the central server 155 at block 725. If the instruction flow requires additional instructions to be performed, then at block 735, the central server 155 selects the next instruction to send and the operations repeat from block 720.

Figure 11A:
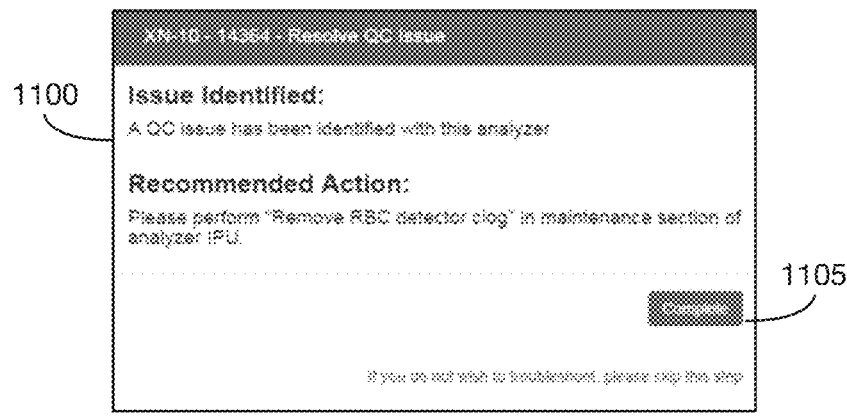

FIG. 11A illustrates a first exemplary troubleshooting instruction window 1100 that may be displayed on one or more of the central computer 108, the tablet 107, or the target diagnostic analyzer 110a that may be communicated in connection with the instruction illustrated at block 768*a* of FIG. 7C. The instruction window 1100 displays the first instruction selected by the central server 155 and communicated to the central computer 108 and/or the tablet 107. The instructions in the exemplary instruction window 1100 ask the operator to perform the operation "Remove RBC detector clog" to unclog an RBC detector of the target diagnostic analyzer 110*a* and to press a completion button 1105 when the operation has been completed. The operator performs this operation by referring to a maintenance manual which is displayed on the screen in response to the operator's request. By reference to the manual, the operator causes the central computer 108, the tablet 107, or the target diagnostic analyzer 110*a* to display a help window which includes a start button for starting the operation to remove an RBC detector clog. In response to the operator's selection of the start button, the target diagnostic analyzer 110*a* may automatically start performing the operation to remove the RBC detector clog. In alternative implementations, the help window including the start button may be displayed on the central computer 108, the tablet 107, or the target diagnostic analyzer 110*a* instead of the window 1100 in response to the instruction illustrated at block 768*a* of FIG. 7C.

Upon pressing the completion button 1105, the operator is presented with a popup window 1110 (FIG. 11B) that prompts the operator to enter his credentials and any comments related to performance of the procedure indicated in the instruction, and to submit the information. Up until this point the central server 155 is waiting for confirmation, as illustrated at block 768*b* of FIG. 7C. Submission of the response is processed by the central server 155 at block 730 of FIG. 7B FIG. 12A illustrates a second exemplary troubleshooting instruction window 1100 that may be displayed on either the central computer 108, the tablet 107, or the target diagnostic analyzer 110*a* that may be communicated in connection with the instruction illustrated at block 754*a* of FIG. 7C. In this regard, the central server 155 may communicate the second instruction to the central computer 108 and/or the tablet 107 upon confirmation that the previous instruction has been performed. The central computer 108 and/or the tablet 107 may in turn update the exemplary instruction window 1100, as illustrated in FIG. 12A, to prompt the user to clean flow passages in the diagnostic analyzer 110*a* such as an RBC detector and a flow cell used for white blood cell measurements and to press a completion button 1105 when the operation has been completed. In alternative implementations, a help window including a start button may be displayed on the central computer 108, the tablet 107, or the target diagnostic analyzer 110*a* instead of the window 1100. In response to the operator's selection of the start button, the target diagnostic analyzer 110*a* may automatically start performing the operation to clean the flow passages in the diagnostic analyzer 110*a*.

Upon pressing the completion button 1105, the operator may once again be presented with a popup window 1110 (FIG. 12B) that prompts the operator to enter his credentials and any comments related to performance of the procedure indicated in the instructions, and to submit the information. Up until this point the central server 155 is waiting for confirmation, as illustrated at block 754*b* of FIG. 7C. Submission of the response is processed by the central server 155 at block 730 of FIG. 7B.

Returning to FIG. 7A, if at block 705 the number of rule 1 violations has exceeded a threshold, such as five, or if at block 700 there are no rule 1 violations, but at block 712, there are other violations, then at block 770 the target diagnostic analyzer 110*a* may be flagged as having trending issues, requiring service, or as having other issues.

At block 775, in some implementations, adjustments for one or more parameters of the target diagnostic analyzer 110*a* may be determined to correct an issue with the target diagnostic analyzer 110*a*. For example, sensitivity and bias adjustments associated with various measurements performed by the target diagnostic analyzer 110*a* may be determined so as to cause the target diagnostic analyzer to generate measurement values for the previously measured QC sample that do not violate any of the rules described above.

At block 777, the central server 155 may report the issue to the central computer 108, the tablet 107, and/or the target diagnostic analyzer 110*a*. For example, the central server 155 may communicate an indication of trending issues to the central computer 108, the tablet 107, and/or target diagnostic analyzer 110*a* to indicate that either the CV and/or mean values associated with the last N or any number of QC measurements is shifting away from the group CV and group mean, respectively. This may warn the operator of an impending problem with the target diagnostic analyzer 110*a*.

In some implementations, the central server 155 may determine, based on the combination rule violations, lot age, maintenance history of the target diagnostic analyzer, etc. that the target diagnostic analyzer requires service. In this case, the central server 155 may communicate instructions to a service agency for servicing the target diagnostic analyzer 110*a*. The instructions may include the parameter adjustments described above.

Under these circumstances, the central server 155 may also communicate instructions to the central computer 108, the tablet 107, and/or target analyzer to automatically disable the target diagnostic analyzer 110 to thereby prevent the target analyzer 110*a* from performing further processing until any issues have been resolved.

If at block 712, there are no other rule violations, then the procedures in FIG. 7A may end.

As previously noted in FIG. 2, if no issues are reported at block 220, then at block 225, the target diagnostic analyzer 110 may be utilized to perform patient sample processing.

As noted above, FIG. 7D illustrates exemplary operations performed by the target diagnostic analyzer 110*a* in cooperation with the operations of FIGS. 7A and 7B performed by the central server 155. At block 780, the target diagnostic analyzer 110*a* may receive an indication that a violation has occurred and may update the display accordingly. For example, the target diagnostic analyzer 715 may initially display the screen illustrated in FIG. 8 and then change to the screen of FIG. 9 to indicate that there is an issue with one of the diagnostic analyzers 110*a*. Where the rule violation is one or more of rules 2-5, the screen may be updated to indicate that there is a trending issue with the target diagnostic analyzer 110*a*. Where there is a rule 1 violation, the screen may be updated to allow an operator to select operations for resolving the issue.

At block 782, if the operator indicates that he would like to start troubleshooting the issue, a trouble shooting request may be communicated to the central server 155.

At block 784, a first instruction for troubleshooting the issue may be received and then displayed. The instruction may correspond to the instruction selected by the central server 155 at block 715. For example, the exemplary instruction illustrated in FIG. 11A may be received and displayed.

At block 786, the target diagnostic analyzer 110*a* may wait until the operator indicates completion of the instruction.

Figure 11B:
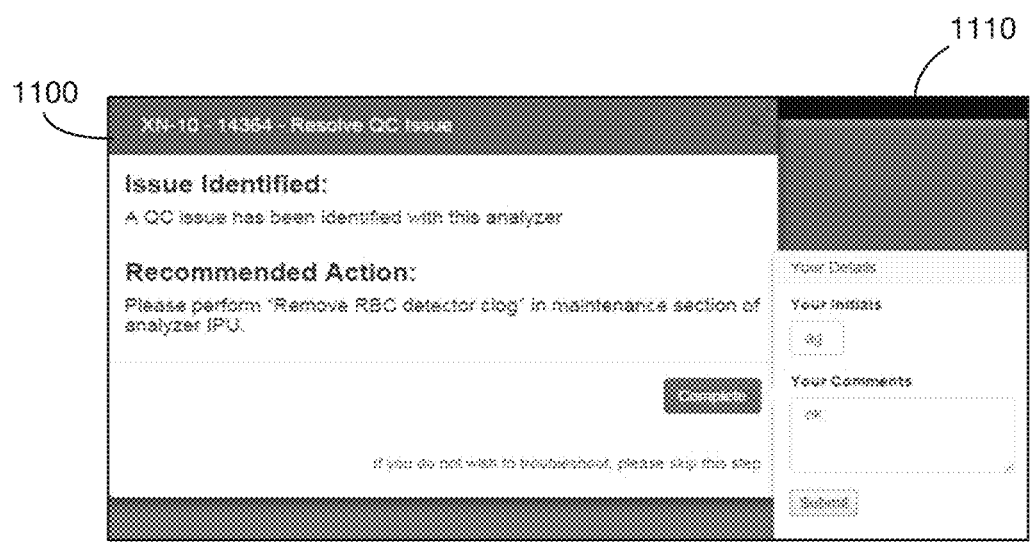
Figure 12A:
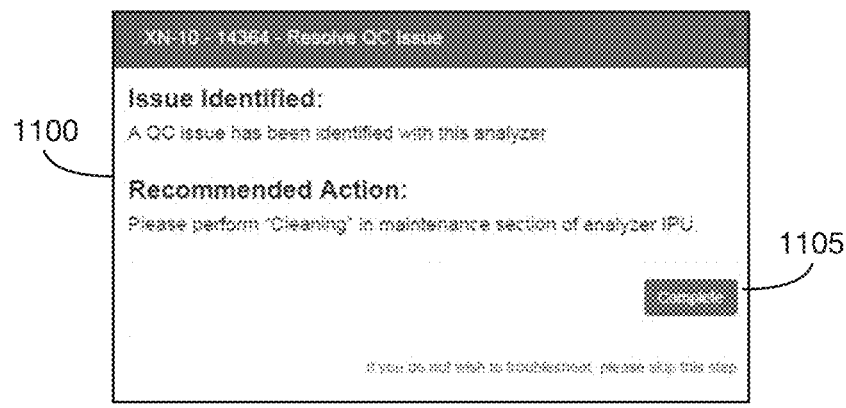
Figure 12B:
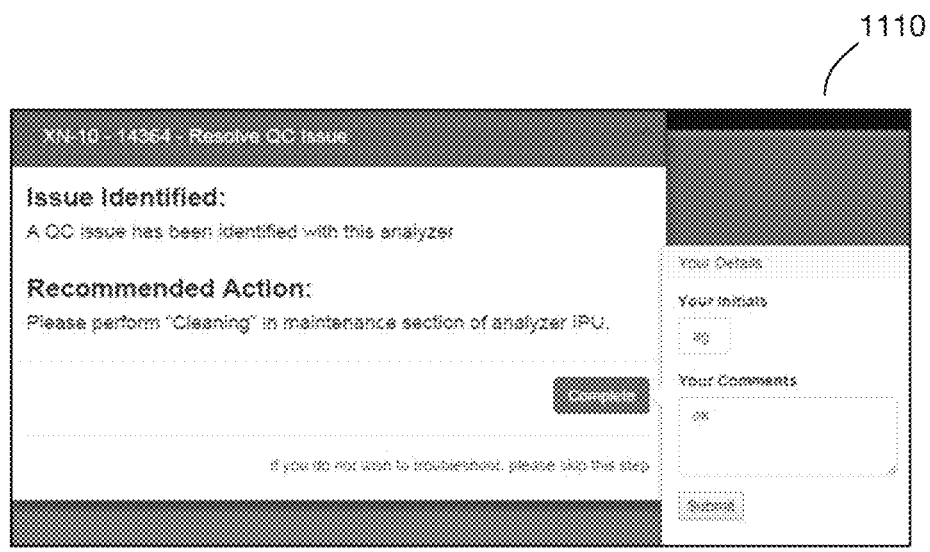

At block 788, the target diagnostic analyzer 110a may require that the operator provide operator information that includes the operator's name and any comments associated with the instruction, as illustrated in FIG. 11B. The target diagnostic analyzer 110a may then communicate the operator information to the central sever 155.

If at block 790, additional instructions are pending, then the operations may repeat from block 784. For example, the instructions illustrated in FIGS. 12A-13 may be communicated.

If all the instructions have been processed, then at block 792, if target analyzer 110a determines, based on an indication from the central server 155 that the issue is resolved, patient sample processing may proceed on the target diagnostic analyzer 110a.

If at block 792, the issue has not been resolved after following various instructions, at block 794, the target diagnostic analyzer 110a may display an indication that service is required and may prevent patient processing from proceeding.

Figure 14:
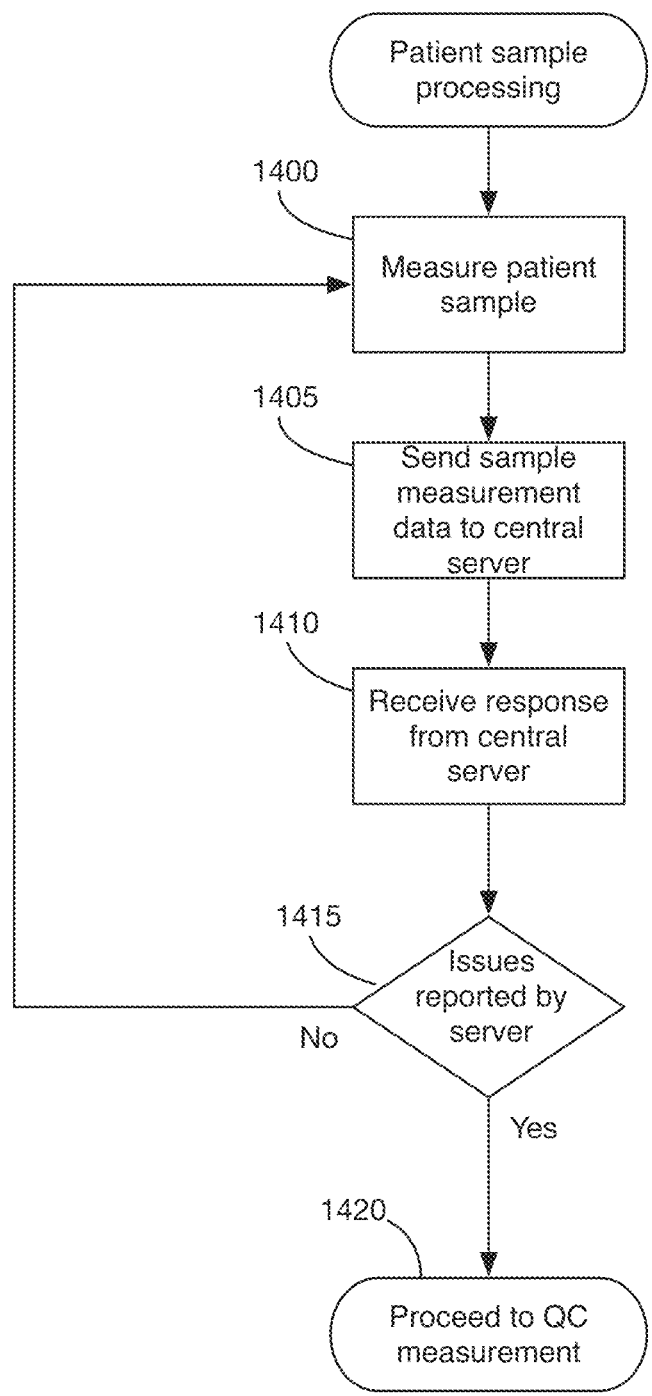
FIG. 14 illustrates exemplary operations that may be performed by the target diagnostic analyzer in processing a patient sample.

FIG. 14 illustrates exemplary operations that may be performed by the target diagnostic analyzer 110 in processing a patient sample. At block 1400, a patient sample measurement may be performed on the target diagnostic analyzer 110a. For example, if QC measurement related issues were not reported by the central server 155, then a message may be displayed on the target diagnostic analyzer 110 instructing an operator to insert a patient sample into the target diagnostic analyzer 110. The target diagnostic analyzer 110 may then measure the quantities of various constituents in the patient sample.

At block 1405, the diagnostic analyzer 110a may communicate the measured values to the central server 155.

At block 1410, the diagnostic analyzer 110a may receive a response associated with the previously communicated patient sample measurements from the central server 155.

If at block 1415, the response indicates that no issues related to the measurements were detected, then the operations may repeat from block 1400.

If at block 1415, the response indicates that there appear to be issues with the measurements and/or the diagnostic analyzer 110a, then at block 1420, the target diagnostic analyzer 110a may be instructed to perform QC measurements as illustrated in FIG. 2.

Figure 15:
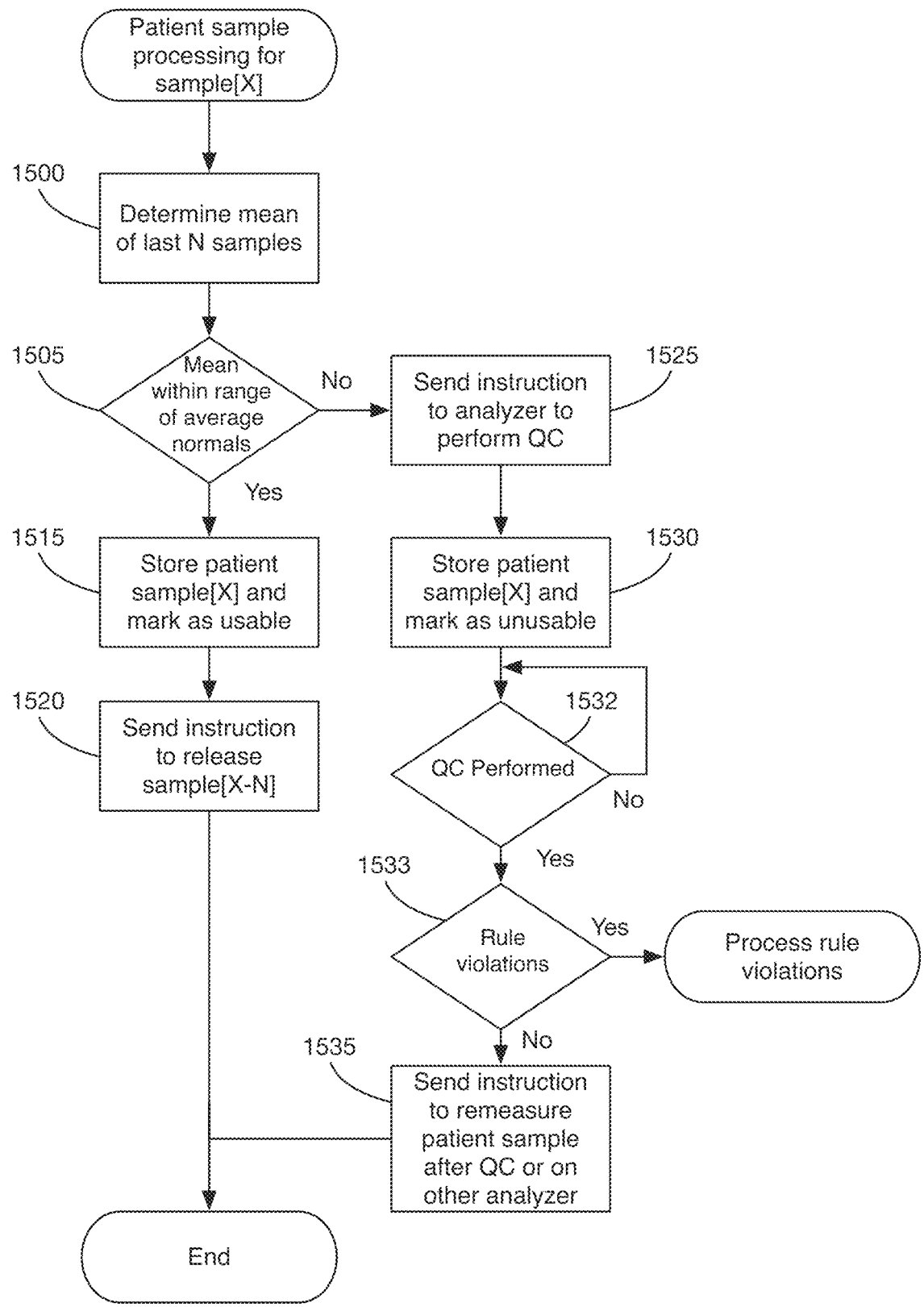
FIG. 15 illustrates exemplary operations that may be performed by the central server upon receipt of a patient sample.

FIG. 15 illustrates exemplary operations that may be performed by the central server 155 upon receipt of measurement data of a patient sample.

At block 1500, the central server 155 may determine the mean values for the quantities of constituents in last N patient samples measured by the target diagnostic analyzer 110a. For example, the mean value for each constituent in the last 10 patient samples may be determined.

At block 1505, the central server 155 may compare the mean value determined above with the mean or so called average normal associated with the quantities of constituents in other patient samples measurements stored in the patient sample database 160. Table 3 below illustrates exemplary records that may be stored in the patient sample database 160.

TABLE 3

| Patient Sample | Useable | RBC | HGB | ... | MCH |
|---|---|---|---|---|---|
| 1 | YES | 2.25 | 5.95 | | 26.45 |
| 2 | YES | 2.28 | 5.8 | | 27.00 |
| 3 | NO | 10.0 | 11 | | 50.00 |
| | ... | | | | |

Referring to Table 3, each record may correspond to a specific patient's sample and may include the quantities of various constituents measured in the sample. In addition, each record may include a Useable parameter that indicates whether a given patient sample may be utilized in determining the mean values associated with the constituent substances of the patient samples. For example, the average normal value for RBC may correspond to the average of values 2.25 and 2.28, which are associated with samples 1 and 2. The value 10.0 from sample 3 may not be utilized in calculating the mean value because the Useable parameter is set to NO.

If at block 1505, the mean values associated with the patient sample received from the target diagnostic analyzer 110a are within a predetermined range such as ±10% of the average normals associated with the patient samples stored in the patient sample database 160, then at block 1515 the central server 155 may store the patient sample measurement data to the patient sample database 160 and mark the Useable parameter as Yes to indicate that the record may be utilized in the determination of the average normals.

At block 1520, the central server 155 may send an instruction to the central computer 108, the tablet 107, and/or target diagnostic analyzer 110a that the information associated with the [X–N]th sample, where X is the most recently measured sample, may be released. For example, where N equals 10, if the current sample (X) corresponds to the $100^{th}$ sample, then the $90^{th}$ sample may be released to a hospital or doctor. The other samples (i.e., samples 91-100) are held (i.e., not released) until additional samples are processed and determinations are made that the mean remains within the average normals. For example, the $91^{st}$ sample will be released when the 101th sample is measured and determinations are made that the mean is still within the average normals.

Returning to block 1505, if the mean values associated with the patient sample received from the target diagnostic analyzer 110a is outside of the predetermined range of the average normals, then at block 1525, the central server 155 may send an indication that an issue has occurred with the measurement to the central computer 108, the tablet 107, and/or the target diagnostic analyzer 110a along with instructions for performing a QC measurement.

At block 1530, the central server 155 may store the patient sample measurement data to the patient sample database 160 and mark the Useable parameter as "No" to indicate that the record may not be utilized in the determination of the average normals.

At block 1532, if the QC measurement has been performed, then if at block 1533, no rule violations have been detected, then at block 1535, the central server 155 may communicate instructions to the central computer 108, the tablet 107, and/or the target diagnostic analyzer 110a to have the patient sample re-measured.

On the other hand, if the QC measurement has been performed and rule violations have been detected, then the procedures for processing the rule violations may be performed.

In an automated environment in which patient samples are automatically routed to different diagnostic analyzers, the central server 155 may communicate instructions to have the patient sample automatically routed to a different diagnostic analyzer for measurement during the time at which the target diagnostic analyzer 110 is stopped and/or busy processing QC measurements to resolve and issue detected at block 1505. For example, the instructions may control the central computer 108 to route the sample to a different diagnostic analyzer until the issue with the target diagnostic analyzer has been resolved.

It should be understood that in some implementations, patient sample measurement data may be received from each of the diagnostic analyzers 110a-g in communication with the central server 155 every time a patient sample is measured. For each patient sample measured, the central server 155 may determine at least one mean value associated with at least one quantity of a constituent of the patient samples. When the mean value does not conform to the statistical criteria, the central server 155 may communicate and indication of measurement problem to the diagnostic analyzer 110a-g associated with the patient sample for which the mean value did not conform to the statistical criteria.

Figure 16:
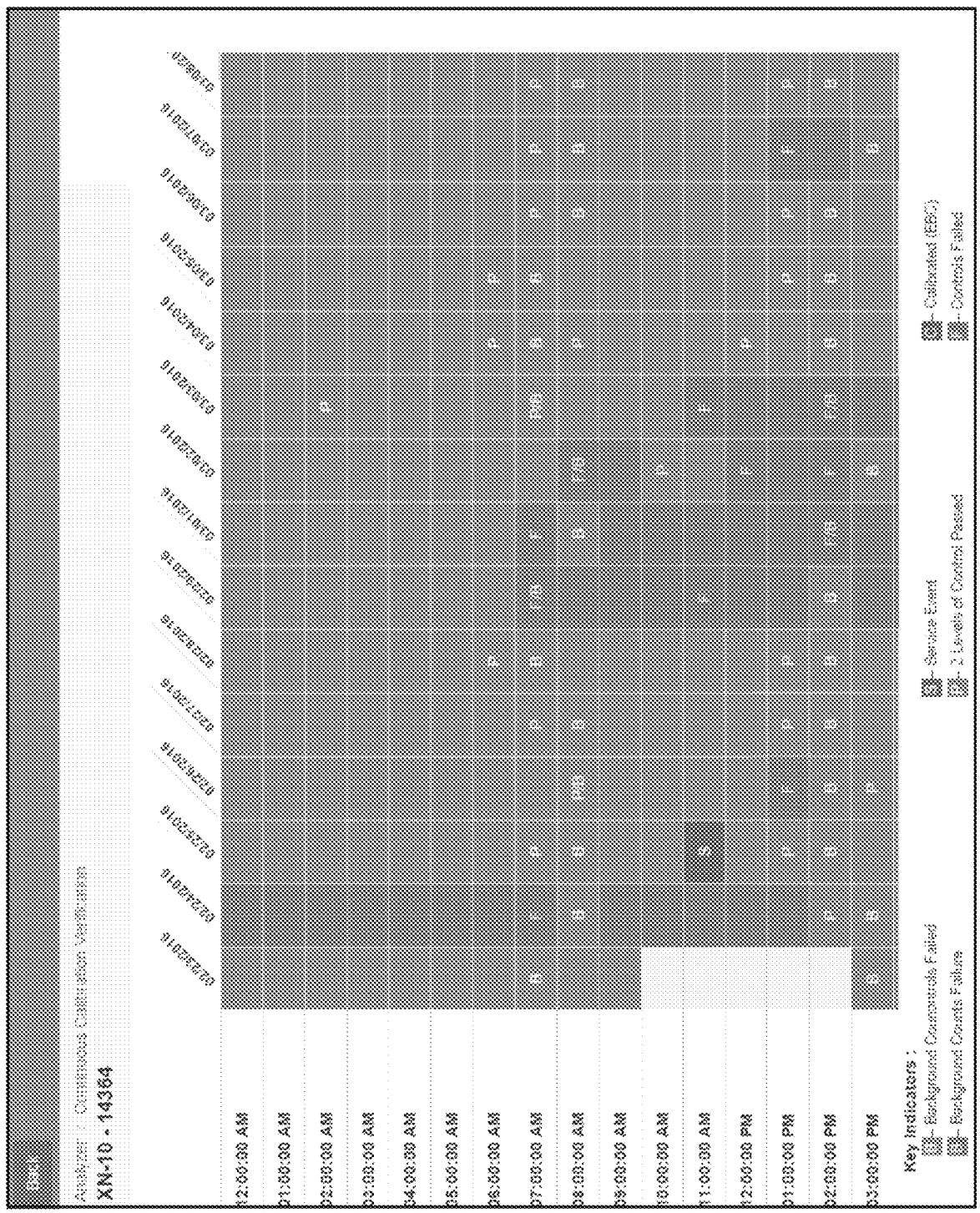
FIG. 16 illustrates an exemplary chart that may be generated by the central server and communicated to the central computer of the laboratory.

FIG. 16 illustrates an exemplary chart 1600 that may be generated by the central server 155 and communicated to the central computer 108 and/or the tablet 107 of the laboratory 105a. The chart 1600 provides an overview of the QC measurement results for a given target diagnostic analyzer 110a over a number of days. Each cell in the chart indicates whether QC measurements were performed at a given time on a given day. The value of the cell indicates the type of measurement, if any, that was performed. An empty cell indicates that no QC measurements were performed. A value of "P" indicates that two levels of QC samples were measured, such as level 1 and level 2 QC samples. A value of "S" indicates that the target diagnostic analyzer 110a was being serviced. A value of "F" indicates that the target diagnostic analyzer 110a failed a QC measurement. A value of "B" indicates a background counts pass. In some implementations, the cells may be color coded to indicate the operational status of the target diagnostic analyzer 110a at a given time and date. For example, a green fill color may be utilized to indicate that the target analyzer 110a was operational. A yellow fill color may be utilized to indicate that the target analyzer 110a was under trending review, meaning that the mean and CV values associated with QC measurements generated by the target analyzer 110a were starting to deviate from the group CV and group mean. A red fill color may be utilized to indicate that the target analyzer 110a was out of service due to an issue of some kind.

Each cell or a subset of the cells in the chart 1600 may be configured to receive a selection from an operator. In one implementation, when the operator selects a cell with the value "P" or pass, the central computer 108 and/or the tablet 107 may generate a request to the central server 155 to generate a continuous calibration verification certificate (CCVC). The CCVC may be utilized by an operator of the laboratory 105a to satisfy regulatory requirements for maintaining reports of the accuracy of a given target diagnostic analyzer 110a. In some implementations, information associated with the operator that requested the report may be communicated to the central server 155 and subsequently stored to a database to thereby obtain a review history associated with the user. For example, a record that relates the operators name, the type of report, and the time the request was made may be stored to the database.

Figure 17:
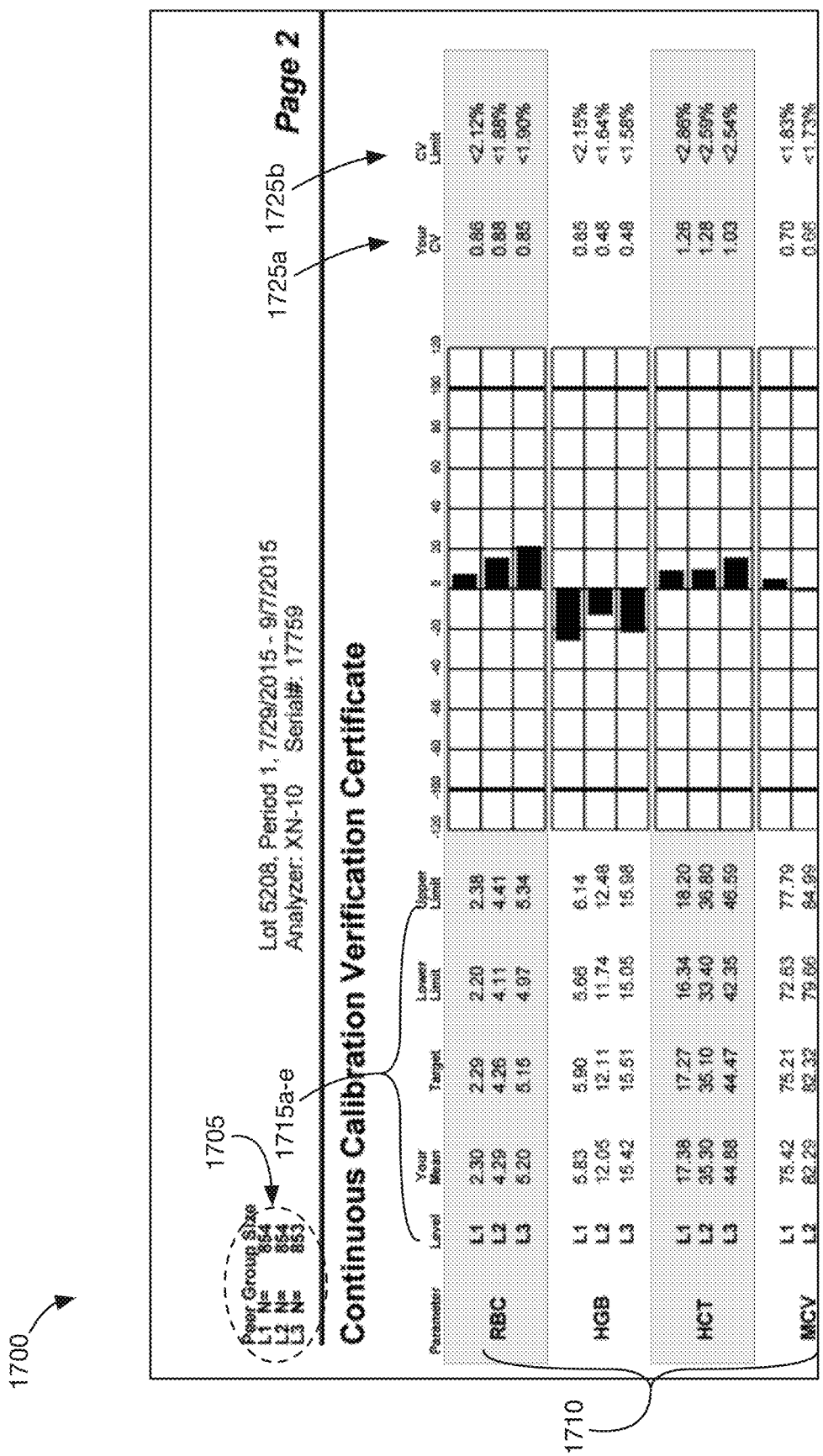
FIG. 17 illustrates an exemplary continuous calibration verification certificate (CCVC)

FIG. 17 illustrates an exemplary continuous calibration verification certificate (CCVC) 1700. The CCVC 1700 includes statistical information associated with the QC measurements performed at the time and day associated with the selected cell along with the group size 1705, from which the group mean and group CV are determined, for each level. For each constituent 1710 in the QC sample, the CCVC specifies the mean value 1715b obtained from the target diagnostic analyzer 110a, target value 1715c which is the group mean, lower limit 1715d, and upper limit 1715e associated with a given QC sample level 1715a. The CV 1725a and CV range 1725b are also specified. A graph 1720 is provided for each constituent and indicates a difference between the mean value 1715b and the target value 1715c. In this graph 1720, the difference is normalized based on the allowable range (TEa*Group Mean) of a given constituent. Specifically, a percentage in the graph 1720 is calculated by the equation [(Your Mean−Group Mean)/(TEa*Group Mean)*100].

Figure 18:
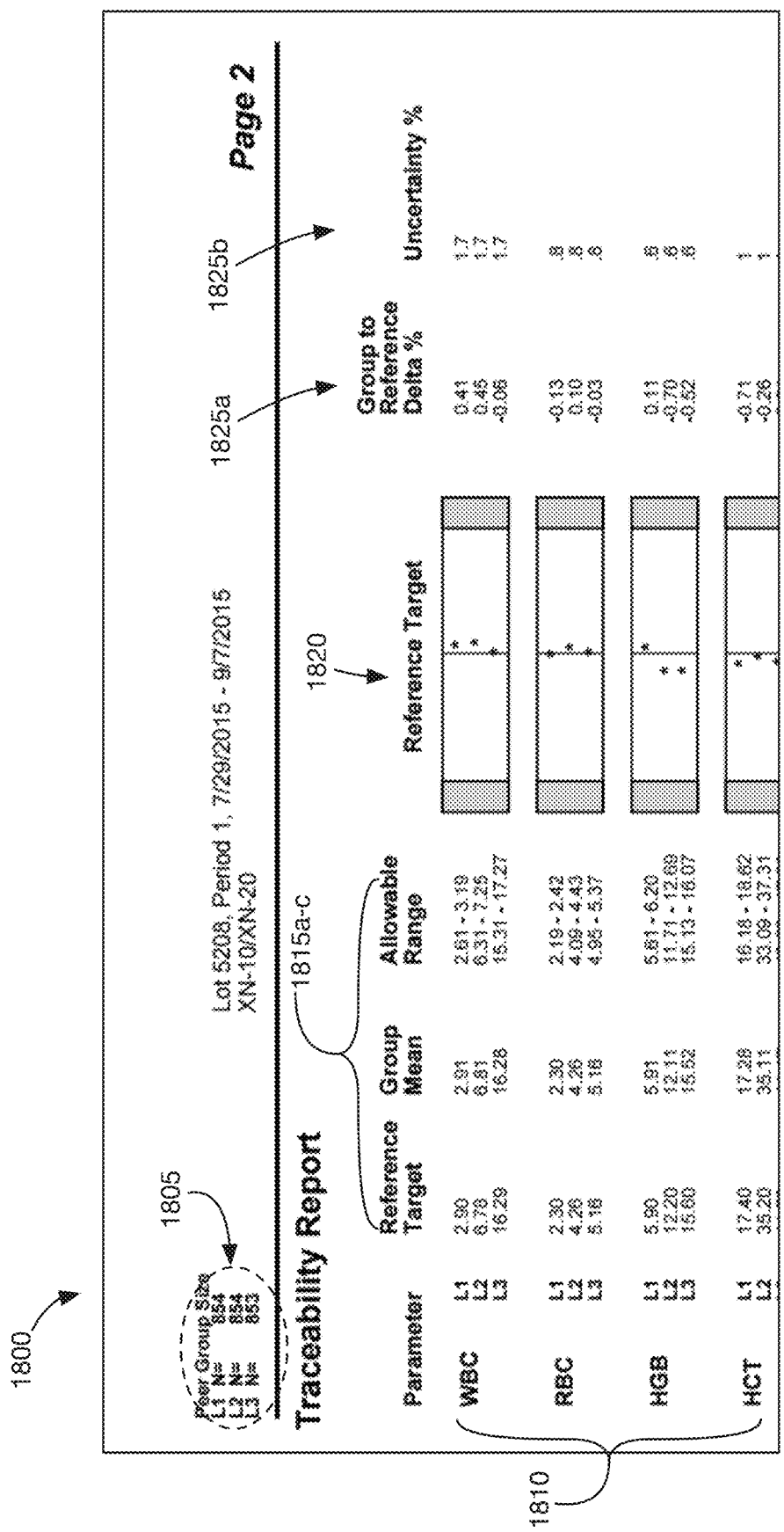
FIG. 18 illustrates an exemplary traceability report that may be generated by the central server in response to a request from the central computer.

FIG. 18 illustrates an exemplary traceability report 1800 that may be generated by the central server 155 in response to a request from the central computer 108 or the tablet 107. The traceability report 1800 defines the various target ranges that are utilized by the central server 155 in determining whether QC measurement received from the target diagnostic analyzer 110a are within an acceptable range.

The traceability report 1800 specifies the group size 1805, from which the group mean and group CV are determined for each level. For each constituent 1810, the traceability report 1800 specifies the reference target 1815a, group mean 1815b, and allowable range 1815c associated with a given constituent 1810. The group mean 1815b is determined via the procedures outlined above.

The reference target 1815a corresponds to the assay target value associated with a given constituent of a given lot. In this regard, the QC samples may be prepared by a third party and delivered to a processing center associated with central service provider 150 for processing. The processing center may use highly calibrated equipment to measure the quantities of the constituents and forward the measurements to the central service provider 150. The target assay values are then set to correspond to the values measured by the processing center.

The traceability report 1800 also provides a graph 1820 that relates the reference target to the group mean to provide a visual representation of the accuracy of the group mean. Other information provided includes the group to reference delta 1825a and the uncertainty percentage 1825b.

Figure 19:
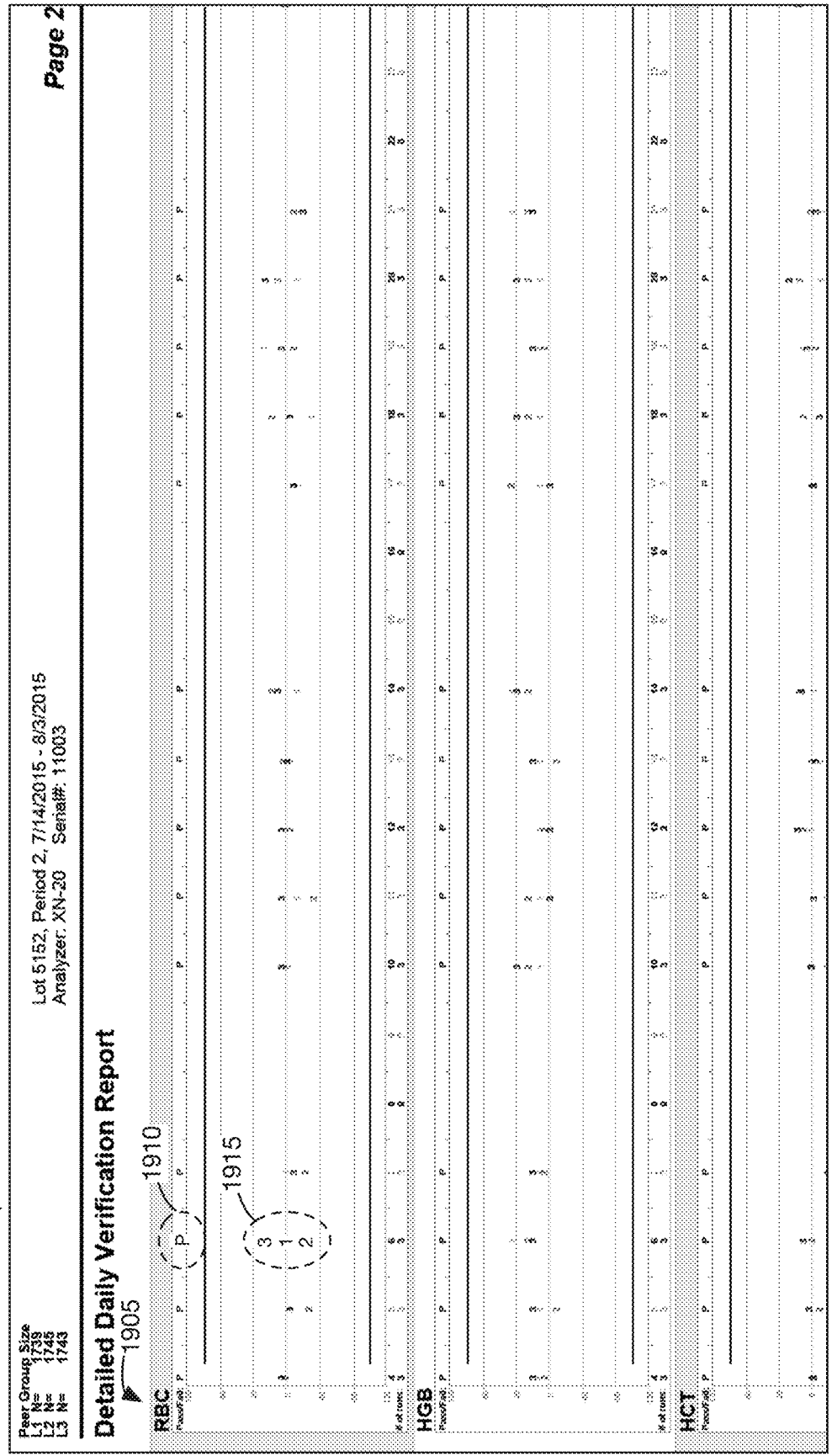
FIG. 19 illustrates an exemplary detailed daily verification report (DDVR)

FIG. 19 illustrates an exemplary detailed daily verification report (DDVR) 1900 that may be generated by the central server 155 in response to a request from the central computer 108 or the tablet 107. The DDVR 1900 shows the results of QC measurements associated with each constituent 1905 of a QC sample taken over the course of a day on a given target diagnostic analyzer 110a. For example, QC measurements 1915 associated with level 1, 2, and 3 samples may be displayed from left to right, in accordance with a time of day that the samples were measured. The vertical placement of the indicator for the level of the QC measurement 1915 indicates the relative value of the measurement. For example, the value for the level 1 RBC measurement in QC measurement 1915 is about zero, which indicates that the level 1 value for the RBC is approximately equal to the group mean associated with RBC measurements for level 1 samples.

FIG. 20 illustrates a general computer system 2000, which may represent or form part of any of the computing devices referenced herein. The computer system 2000 may include a set of instructions 2045 that may be executed to cause the computer system 2000 to perform any one or more of the methods or computer-based functions disclosed herein. The computer system 2000 may operate as a stand-alone device or may be connected, e.g., using a network, to other computer systems or peripheral devices.

In a networked deployment, the computer system 2000 may operate in the capacity of a server or as a client-operator computer in a server-client operator network environment, or as a peer computer system in a peer-to-peer (or distributed) network environment. The computer system 2000 may also be implemented as or incorporated into various devices, such as a personal computer or a mobile device, capable of executing a set of instructions 2045 (sequential or otherwise) that specify actions to be taken by that machine. Further, each of the systems described may include any collection of sub-systems that individually or jointly execute a set, or multiple sets, of instructions to perform one or more computer functions.

The computer system 2000 may include one or more memory devices 2010 on a bus for communicating information, such as any of the database described throughout the application. In addition, code operable to cause the computer system to perform any of the acts or operations described herein may be stored in the memory 2010. The memory 2010 may be a random-access memory, read-only memory, programmable memory, hard disk drive or any other type of memory or storage device.

The computer system 2000 may include a display 2030, such as a liquid crystal display (LCD), a cathode ray tube (CRT), or any other display suitable for conveying information. The display 2030 may act as an interface for the operator to see the functioning of the processor 2005, or specifically as an interface with the software stored in the memory 2010 or in the drive unit 2015.

Additionally, the computer system 2000 may include an input device 2025, such as a keyboard or mouse, configured to allow an operator to interact with any of the components of system 2000.

The computer system 2000 may also include a disk or optical drive unit 2015. The disk drive unit 2015 may include a computer-readable medium 2040 in which one or more sets of instructions 2045, e.g. software, can be embedded. Further, the instructions 2045 may perform one or more of the operations as described herein. The instructions 2045 may reside completely, or at least partially, within the memory 2010 and/or within the processor 2005 during execution by the computer system 2000. The memory 2010 and the processor 2005 also may include computer-readable media as discussed above.

The computer system 2000 may include a communication interface 2035 that enables communications via a network 2050. The network 2050 may include wired networks, wireless networks, or combinations thereof. The communication interface 2035 network may enable communications via any number of communication standards, such as 802.11, 802.12, 802.20, WiMax, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

While the method and system has been described with reference to certain embodiments, it will be understood by those skilled in the art that various changes may be made and equivalents may be substituted without departing from the scope. For example, according to the embodiments above, the central server 155 generates the statistical criteria, determines whether there are issues with a measurement value, and communicates instructions to the target diagnostic analyzer 110a for troubleshooting the issue. In alternative implementations, the target diagnostic analyzer 110a may receive the statistical criteria from the central server 155. The target diagnostic analyzer 110a may then control the measurement hardware to measure a quantity of at least one constituent of the quality control sample and may compare the measurement value with the statistical criteria to determine whether any rule violations have occurred. The target diagnostic analyzer 110a may display a comparison result associated with the determination above via the user interface. In performing the operations above, the target diagnostic analyzer 110a may perform one or more of the operations in FIGS. 3, 4, 7A-7D, and 15 that are performed by the central server 155 in the other described embodiments.

It should also be understood that many modifications may be made to adapt a particular situation or material to the teachings without departing from its scope. Therefore, it is intended that the present method and system not be limited to the particular embodiment disclosed, but that the method and system include all embodiments falling within the scope of the appended claims.

I claim:

1. A method for quality assurance of a sample analyzer, comprising:
providing a statistical criterion for quality assurance of sample analyzers,
the criterion being created based on a peer group data including a plurality of quality control (QC) measurements generated by running tests on quality control samples on a plurality of sample analyzers in a peer group, and
the criterion including a range having an upper limit and a lower limit comparable with a QC measurement generated by a sample analyzer;
comparing, with the range of the statistical criterion, a target QC measurement generated by running a test on a quality control sample on a target sample analyzer; and
displaying, in response to the target QC measurement being outside of the range, on the target sample analyzer or a computer of a laboratory, a screen showing that the target sample analyzer failed to pass the statistical criterion.

2. The method according to claim 1, further comprising adding, in response to the target QC measurement being inside of the range, the target QC measurement in the peer group data; and updating the statistical criterion based on the peer group data including the target QC measurement.

3. The method according to claim 1, wherein the peer group data includes QC measurement generated by running tests on quality control samples of a same lot number.

4. The method according to claim 1, wherein the screen further includes a trouble shooting instruction to solve a problem of the target sample analyzer.

5. The method according to claim 1, further comprising: determining a type of abnormality associated with the target QC measurement.

6. The method according to claim 1, further comprising: providing a troubleshooting instruction based on the type of abnormality.

7. The method according to claim 1, further comprising generating a service request for the target sample analyzer.

8. The method according to claim 1, wherein the target QC measurement includes:
a first QC measurement which is generated by running test on a first quality control sample having a first level of constituents; and
a second QC measurement which is generated by running test on a second quality control sample having a second level of constituents.

9. The method according to claim 8, further comprising comparing the first and second QC measurements with the statistical criterion.

10. The method according to claim 9, further comprising issuing a calibration verification certificate associated with the target sample analyzer in response to both of the first and second QC measurement in the target QC measurement conforming with the statistical criterion.

11. The method according to claim 1, wherein the plurality of sample analyzers are located in geographically distributed facilities.

12. The method according to claim 11, further comprising consolidating QC measurements from the sample analyzers in the peer group over network.

13. The method according to claim 12, further comprising storing the QC measurements in a peer group database at a central server.

14. The method according to claim 13, further comprising receiving the target QC measurement from the target sample analyzer over network at the central server.

15. The method according to claim 1, further comprising updating the statistical criterion on a periodic basis, wherein the QC measurement generated by the target sample analyzer is compared with the latest statistical criterion.

16. The method according to claim 1, wherein the sample analyzer comprises a flow cytometer.

17. The method according to claim 16, further comprising adding, in response to the target QC measurement being inside of the range, the target QC measurement in the peer group data; and
updating the statistical criterion based on the peer group data including the target QC measurement.

18. The method according to claim 16, wherein the peer group data includes QC measurement generated by running tests on quality control samples of a same lot number.

19. The method according to claim 1, wherein the sample analyzer is an automated cell counter.

20. A method for quality assurance of a sample analyzer, comprising:
providing a statistical criterion for quality assurance of sample analyzers,
the criterion being created based on a peer group data including a plurality of quality control (QC) measurements generated by running tests on quality control samples on a plurality of sample analyzers in a peer group, and
the criterion including a range having an upper limit and a lower limit comparable with a QC measurement generated by a sample analyzer;
comparing, with the range of the statistical criterion, a target QC measurement generated by running a test on a quality control sample on a target sample analyzer; and
determining whether the target sample analyzer passes the statistical criterion, based on the comparing.

21. A method for quality assurance of a sample analyzer, comprising:
providing a statistical criterion for quality assurance of sample analyzers,
the criterion being created based on a peer group data including a plurality of quality control (QC) measurements generated by running tests on quality control samples on a plurality of sample analyzers in a peer group, and
the criterion including a range having an upper limit and a lower limit comparable with a QC measurement generated by a sample analyzer;
comparing, with the range of the statistical criterion, a target QC measurement generated by running a test on a quality control sample on a target sample analyzer; and
providing a guidance of trouble shooting, in response to the target QC measurement being outside of the range, on the target sample analyzer.

* * * * *